US011478297B2

(12) United States Patent
Viswanadha et al.

(10) Patent No.: US 11,478,297 B2
(45) Date of Patent: Oct. 25, 2022

(54) SYSTEM AND METHOD FOR CONTROLLING ENERGY DELIVERED TO AN AREA OF TISSUE DURING A TREATMENT PROCEDURE

(71) Applicant: Avent, Inc., Alpharetta, GA (US)

(72) Inventors: Rasagnya M. Viswanadha, Cumming, GA (US); Alenda V. Washington, Roswell, GA (US); Sherry E. Adesina, Tucker, GA (US); Shyamant R. Sastry, Suwanee, GA (US); Jacques P. Mayeux, Alpharetta, GA (US); Craig F. Steinman, Cumming, GA (US); Christa Zachariah, Lawrenceville, GA (US); Petrina Barnett Naylor, Decatur, GA (US)

(73) Assignee: Avent, Inc., Alpharetta, GA (US)

( * ) Notice: Subject to any disclaimer, the term of this patent is extended or adjusted under 35 U.S.C. 154(b) by 554 days.

(21) Appl. No.: 16/363,532

(22) Filed: Mar. 25, 2019

(65) Prior Publication Data

US 2019/0290352 A1    Sep. 26, 2019

Related U.S. Application Data

(60) Provisional application No. 62/722,610, filed on Aug. 24, 2018, provisional application No. 62/647,222, filed on Mar. 23, 2018.

(51) Int. Cl.
*A61B 18/14* (2006.01)
*A61N 1/06* (2006.01)
(Continued)

(52) U.S. Cl.
CPC .............. *A61B 18/148* (2013.01); *A61N 1/06* (2013.01); *A61B 2018/00005* (2013.01);
(Continued)

(58) Field of Classification Search
CPC ........ A61B 18/148; A61B 2018/00577; A61B 2018/00702; A61B 2018/00589;
(Continued)

(56) References Cited

U.S. PATENT DOCUMENTS 7,163,536 B2    1/2007   Ara et al.
7,258,688 B1    8/2007   Shah et al.
(Continued)

FOREIGN PATENT DOCUMENTS

WO    2016/198626    12/2016

OTHER PUBLICATIONS

Nir Rozenblum, Radiofrequency Ablation: Inflammatory Changes in the Periablative Zone Can Induce Global Organ Effects, including Liver Regeneration, 2015, RSNA, vol. 2, 416-425 (Year: 2015).*
(Continued)

*Primary Examiner* — Joanne M Hoffman
*Assistant Examiner* — Sean W Collins
(74) *Attorney, Agent, or Firm* — Meunier Carlin & Curfman LLC

(57) ABSTRACT

Systems and methods for controlling energy delivered to an area of tissue during a treatment procedure are provided. The system includes a device for delivering energy to the area of tissue; an energy generator for generating and supplying energy to the device; and a controller for controlling an amount of energy generated by the energy generator and delivered to the area of tissue by the device. Controlling the amount of energy delivered to the area of tissue alters a primary zone of the area of tissue to a first level, alters a secondary zone to a second level, alters a tertiary zone to a third level, or a combination thereof, where the first level, the second level, the third level, or a combination thereof is predetermined, and where a coverage area of the primary
(Continued)

zone, the secondary zone, the tertiary zone, or a combination thereof is also predetermined.

**18 Claims, 26 Drawing Sheets
(8 of 26 Drawing Sheet(s) Filed in Color)**

(51) Int. Cl.
*A61N 1/36* (2006.01)
*A61B 18/00* (2006.01)
*A61B 34/10* (2016.01)

(52) U.S. Cl.
CPC .............. *A61B 2018/00023* (2013.01); *A61B 2018/00434* (2013.01); *A61B 2018/00577* (2013.01); *A61B 2018/00589* (2013.01); *A61B 2018/00702* (2013.01); *A61B 2018/00744* (2013.01); *A61B 2034/104* (2016.02); *A61N 1/36021* (2013.01)

(58) Field of Classification Search
CPC ........... A61B 2018/00434; A61B 2018/00005; A61B 2018/00023; A61B 2018/00791; A61B 2090/064; A61B 2018/00642; A61B 2018/00744; A61B 18/1206; A61N 1/06; A61N 1/36021
USPC ......................................................... 606/34
See application file for complete search history.

(56) References Cited

U.S. PATENT DOCUMENTS

| | | | |
|---|---|---|---|
| 7,593,778 B2 | 9/2009 | Chandran et al. | |
| 7,819,869 B2 | 10/2010 | Ara et al. | |
| 8,882,755 B2 | 11/2014 | Leung et al. | |
| 9,993,294 B2* | 6/2018 | Turner | A61B 18/1815 |
| 2003/0097130 A1* | 5/2003 | Muller | A61B 18/14 606/41 |
| 2004/0176759 A1 | 9/2004 | Krishnamurthy | |
| 2005/0049582 A1* | 3/2005 | DeBenedictis | A61B 18/20 606/9 |
| 2005/0177209 A1 | 8/2005 | Leung et al. | |
| 2006/0155266 A1 | 7/2006 | Manstein et al. | |
| 2006/0195076 A1 | 8/2006 | Blumenkranz et al. | |
| 2007/0156136 A1 | 7/2007 | Godara et al. | |
| 2009/0024124 A1 | 1/2009 | Lefler et al. | |
| 2011/0118724 A1* | 5/2011 | Turner | A61B 18/1815 606/33 |
| 2013/0090646 A1* | 4/2013 | Moss | A61B 18/1487 606/41 |
| 2013/0289369 A1 | 10/2013 | Margolis | |
| 2013/0324989 A1* | 12/2013 | Leung | A61B 90/11 606/24 |
| 2014/0058387 A1 | 2/2014 | Kruecker et al. | |
| 2015/0018725 A1 | 1/2015 | Sommer | |
| 2015/0335381 A1* | 11/2015 | Hlavka | A61B 18/1485 606/41 |
| 2016/0008635 A1 | 1/2016 | Burdete et al. | |
| 2017/0065348 A1 | 3/2017 | Fish et al. | |
| 2017/0181788 A1 | 6/2017 | Dastjerdi et al. | |
| 2017/0231693 A1 | 8/2017 | Nelson et al. | |
| 2017/0238993 A1* | 8/2017 | Curley | A61B 18/082 |
| 2017/0348049 A1* | 12/2017 | Vrba | A61B 18/1492 |

OTHER PUBLICATIONS

Kunio Takeda, Conformational Change of Bovine Serum Albumin by Heat Treatment, Journal of Protein Chemistry, 1989, vol. 8, 653-659 (Year: 1989).*
IFST, Protein: Coagulation, 2017 (Year: 2017).*
Thomas A. Holme, Denaturation, 2006 (Year: 2006).*
Chaplan et al. Quantitative assessment of tactile allodynia in the rat paw. J Neurosci Methods. Jul. 1994;53(1):55-63.
Choi, Samjin, et al. "Internal-specific morphological analysis of sciatic nerve fibers in a radiofrequency-induced animal neuropathic pain model." PloS one 8.9 (2013): e73913.
Davis, Tim, et al. "Prospective, multicenter, randomized, crossover clinical trial comparing the safety and effectiveness of cooled radiofrequency ablation with corticosteroid injection in the management of knee pain from osteoarthritis." Reg Anesth Pain Med 43.1 (2018): 84-91.
English et al. Recovery of electromyographic activity after transection and surgical repair of the rat sciatic nerve. J Neurophysiol. Feb. 2007;97(2):1127-34. Epub Nov. 22, 2006.
Halyard Health Announces New Data Supporting COOLIEF* Cooled rf for the Treatment of Chronic Osteoarthritis Knee Pain. Sep. 18, 2017. 3 pages, available on-line at https://www.prnewswire.com/news-releases/halyard-health-announces-new-data-supporting-coolief-cooled-rf-for-the-treatment-of-chronic-osteoardiritis-knee-pain-300520689.html.
Han et al. Facilitation of synaptic transmission and pain responses by CGRP in the amygdala of normal rats. Mol Pain. Feb. 8, 2010;6:10. doi: 10.1186/1744-8069-6-10.
Larson et al. Pain threshold changes in adjuvant-induced inflammation: a possible model of chronic pain in the mouse. Pharmacol Biochem Behav. Jan. 1986;24(1):49-53.
Vania Apkarian et al. Neural mechanisms of pain and alcohol dependence. Pharmacol Biochem Behav. Nov. 2013; 112: 34-41.
Crone T, video, "What is cooled radiofrequency? The physics of RF ablation." available online at https://www.cooledrf.london/what-is-coolief-new.html (last accessed Aug. 24, 2018).
English, A., Provenzano, D., Adesina, S., Zachariah, C., Mayeux, J., Alas, G., Lightner, K., Mistretta, O., Ward, P., Chen, A. and Washington, A. (2018). Cooled RF Ablation Produces Enhanced Thermal Lesions and Greater Reduction in Nerve Function. ASRA, San Antonio, Texas Presented Nov. 2018, 1 page. available on-line at: https://epostersonline.com/ASRAFALL18/node/769.
Zachariah, et al., Cooled Radiofrequency Ablation Produces Enhanced Thermal Lesions In Vivo, ORS Annual Meeting, Austin, Texas Presented Feb. 2019, 1 page.
Mayeux, et al., Cooled Radiofrequency Ablation Provides Extended Brain and Behavior Benefits in a Rodent Model of Pain, presented at the Orthopedic Research Society meeting in Austin, TX on Feb. 3, 2019, Poster, 1 page.
International Search Report and Written Opinion dated Jun. 14, 2019, from International Application No. PCT/US2019/023870, 9 pages.
Extended European Search Report dated Nov. 25, 2021, from EP Application No. 19772201.0, 9 pages.

* cited by examiner

SYSTEM AND METHOD FOR CONTROLLING ENERGY DELIVERED TO AN AREA OF TISSUE DURING A TREATMENT PROCEDURE

CROSS REFERENCE TO RELATED APPLICATIONS

This application claims the benefit of U.S. Provisional Application No. 62/722,610, filed Aug. 24, 2018 and U.S. Provisional Application No. 62/647,222, filed Mar. 23, 2018. Each of these applications is incorporated by reference in their entireties for all purposes.

FIELD

This application relates to pain management, and more specifically, to radiofrequency ablation of a target tissue.

BACKGROUND OF THE INVENTION

Certain types of chronic pain, for example, pain stemming from knee osteoarthritis (OA), can be effectively managed by radiofrequency ablation (RFA) of the sensory genicular nerves in the knee. RFA is a non-opioid, minimally invasive thermal ablation procedure that is hypothesized to provide pain relief by temporarily blocking signaling of the pain-transmitting sensory nerves and eliminating perception of pain in the central nervous system. This provides both physical and psychological relief to the patient. Radiofrequency energy and other types of energy can also be used to ablate, denervate, or otherwise alter tissue (i.e., nerve tissue such as peripheral nerve tissue, cardiac muscle tissue, renal tissue, pulmonary tissue, connective tissue, skeletal muscle tissue, etc.) during other medical or veterinary procedures to treat a condition or relieve pain.

Despite the promise of radiofrequency energy-based treatments, there is no reliable technique for controlling the energy delivered to the tissue, which means that the area or extent of tissue alteration may be larger than needed, which can waste energy and damage tissue unnecessarily. Alternatively, the area or extent of tissue alteration can be too small, which result in an ineffective treatment procedure. In addition, in some cases, the energy delivered can form a physical lesion in the tissue, where the formation of the physical lesion may not be needed for a treatment procedure to be effective. In ex vivo tissue models, physicians and health practitioners typically correlate an area of tissue exhibiting substantial coagulation of proteins visible to the unaided eye resulting from the application of energy as an approximation for the region of effective tissue alteration, ablation, or denervation, where a physical lesion is visible. For example, ablation procedures are typically modeled utilizing non-perfuse and non-nervous tissue such as in a chicken breast and the resulting visible lesion is correlated with the area of protein coagulation to determine the area of effective ablation. However, in a patient treatment setting, there is a need for an improved system and method for controlling the energy delivered in a predetermined fashion so that the desired level of tissue alteration, ablation, or denervation during the treatment procedure can be realized while minimizing unnecessary tissue damage, minimizing discomfort to the patient, and minimizing energy usage.

SUMMARY

Objects and advantages of the systems and methods disclosed herein will be set forth in part in the following description, or may be obvious from the description, or may be learned through practice of the invention. The invention will be described in greater detail below by reference to embodiments thereof illustrated in the figures.

In one particular embodiment, a system for controlling energy delivered to a treatment area (e.g., an area of tissue) during a treatment procedure is provided. The system includes a device for delivering energy to the area of tissue; an energy generator for generating and supplying energy to the device; and a controller for controlling an amount of energy generated by the energy generator and delivered to the area of tissue by the device, wherein controlling the amount of energy delivered to the area of tissue alters a primary zone of the area of tissue to a first level, alters a secondary zone of the area of tissue to a second level, alters a tertiary zone of the area of tissue to a third level, or a combination thereof, wherein the first level, the second level, the third level, or a combination thereof is predetermined, and wherein a coverage area of the primary zone, the secondary zone, the tertiary zone, or a combination thereof is predetermined.

In one system embodiment, the device for applying energy to the area of tissue can be a probe, such as a percutaneous probe.

In another system embodiment, the treatment procedure can be a medical procedure or a veterinary procedure.

In still another system embodiment, the system can be configured to deliver from about 25 joules to about 100 kilojoules of energy to the area of tissue.

In yet another system embodiment, the energy can be radiofrequency energy.

Further, the probe can be a cooled radiofrequency probe. The probe can include a sensing device that sends a signal to the controller for controlling an amount of energy generated and/or operation of a cooling mechanism of the cooled radiofrequency probe to adjust a property of the probe and/or the area of the tissue. The sensing device can be, for example, a temperature sensing device, an impedance measuring means, or a pressure sensor.

In one more system embodiment, the area of tissue can include nerve tissue, cardiac muscle tissue, renal tissue, pulmonary tissue, connective tissue, skeletal muscle tissue, or a combination thereof.

In an additional system embodiment, the primary zone can be adjacent the device, the secondary zone can be adjacent the primary zone, and the tertiary zone can be adjacent the secondary zone.

In one system embodiment, the first level of tissue alteration is associated with from 75 percent to 100 percent coagulation of proteins, the second level of tissue alteration is associated with from 25 percent to less than 75 percent coagulation of proteins, and the third level of tissue alteration is associated with greater than 0 percent but less than 25 percent coagulation of proteins.

In one system embodiment, the coverage area for the primary zone, the secondary zone, the tertiary zone, or a combination thereof can be determined via a relationship between the amount of energy delivered to the area of tissue, an amount of time during which the energy is delivered, a waveform type, device placement, device location, device dimensions, surgical approach, a temperature at which the energy is delivered, or a combination thereof.

In another system embodiment, the first level, the second level, the third level, or a combination thereof can be determined via a relationship between an amount of energy delivered to the area of tissue, an amount of time during which the energy is delivered, a waveform type, device placement, device location, device dimensions, surgical approach, a temperature at which the energy is delivered, or a combination thereof.

In still another system embodiment, the first level can correspond to a greater extent of tissue alteration, cell type alteration, biochemical signaling alteration, or a combination thereof compared to the second level, and the second level can correspond to a greater extent of tissue alteration cell type alteration, biochemical signaling alteration, or a combination thereof compared to the third level.

In yet another system embodiment, the secondary zone can increase the area of coverage of the primary zone by a factor ranging from about 1.25 to about 15.

In one more system embodiment, the treatment procedure can be a denervation procedure, wherein a physical lesion associated with denervation can be induced by the system in the primary zone, wherein a lesser extent of denervation can be induced by the system in the secondary zone compared to the primary zone, wherein one or more biochemical changes and/or physiological responses can be induced by the system in the tertiary zone, or a combination thereof. Further, the one or more biochemical changes and/or physiological responses can include changes in levels of perineurial collagen coagulation, epineurial collagen coagulation, endoneurial collagen coagulation, coagulative necrosis, vascular necrosis, axonal degeneration, inflammation, subacute histiocytosis, hypertrophy, hyperplasia, immune cell activation, schwann cell infiltration, nerve fibrosis, macrophage infiltration, growth cone sprouting, structural integrity, sensory threshold, biochemical signaling, cell body response, dorsal root ganglia response, or a combination thereof.

In an additional system embodiment, the system can provide pain relief to a subject.

In another particular embodiment, a method for controlling energy delivered to an area of tissue during a treatment procedure is provided. The method includes the steps of: inserting a device for delivering energy adjacent the area of tissue to be treated; generating and supplying energy to the device via an energy generator; and controlling an amount of energy generated by the energy generator and delivered to the area of tissue by the device via a controller, wherein controlling the energy delivered to the area of tissue alters a primary zone of the area of tissue to a first level, alters a secondary zone of the area of tissue to a second level, alters a tertiary zone of the area of tissue to a third level, or a combination thereof, wherein the first level, the second level, the third level, or a combination thereof is predetermined, and wherein a coverage area of the primary zone, the secondary zone, the tertiary zone, or a combination thereof is predetermined.

In one method embodiment, the device for applying energy to the area of tissue can be a probe, such as a percutaneous probe.

In another method embodiment, the treatment procedure can be a medical procedure or a veterinary procedure.

Another method embodiment further includes delivering from about 25 joules to about 100 kilojoules of energy to the area of tissue.

In yet another method embodiment, the energy can be radiofrequency energy. Further, the probe can be a cooled radiofrequency probe. The method can include sending a signal from the sensing device to the controller for controlling an amount of energy generated and/or operation of a cooling mechanism of the cooled radiofrequency probe to adjust a property of the probe and/or the area of the tissue. The sensing device can be, for example, a temperature sensing device, an impedance measuring means, or a pressure sensor.

In one more method embodiment, the area of tissue can include nerve tissue, cardiac muscle tissue, renal tissue, pulmonary tissue, connective tissue, skeletal muscle tissue, or a combination thereof.

In an additional method embodiment, the primary zone can be adjacent the device, the secondary zone can be adjacent the primary zone, and the tertiary zone can be adjacent the secondary zone.

In one method embodiment, the first level of tissue alteration is associated with from 75 percent to 100 percent coagulation of proteins, the second level of tissue alteration is associated with from 25 percent to less than 75 percent coagulation of proteins, and the third level of tissue alteration is associated with greater than 0 percent but less than 25 percent coagulation of proteins.

Another method embodiment further comprises determining the coverage area for the primary zone, the secondary zone, the tertiary zone, or a combination thereof based on a relationship between the amount of energy delivered to the area of tissue, an amount of time during which the energy is delivered, a waveform type, device placement, device location, device dimensions, surgical approach, a temperature at which the energy is delivered, or a combination thereof.

Another method embodiment further comprises determining the first level, the second level, the third level, or a combination thereof based on a relationship between the amount of energy delivered to the area of tissue, an amount of time during which the energy is delivered, a waveform type, device placement, device location, device dimensions, surgical approach, a temperature at which the energy is delivered, or a combination thereof.

In still another method embodiment, the first level can correspond to a greater extent of tissue alteration, cell type alteration, biochemical signaling alteration, or a combination thereof compared to the second level, and the second level can correspond to a greater extent of tissue alteration cell type alteration, biochemical signaling alteration, or a combination thereof compared to the third level.

In yet another method embodiment, the secondary zone can increase the area of effective denervation of the primary zone by a factor ranging from about 1.25 to about 15.

In one more method embodiment, the treatment procedure can be a denervation procedure, and can further comprise inducing a physical lesion associated with denervation in the primary zone, inducing a lesser extent of denervation in the secondary zone compared to the primary zone, inducing one or more biochemical changes and/or physiological responses in the tertiary zone, or a combination thereof. Further, the one or more biochemical changes and/or physiological responses can include changes in levels of perineurial collagen coagulation, epineurial collagen coagulation, endoneurial collagen coagulation, coagulative necrosis, vascular necrosis, axonal degeneration, inflammation, subacute histiocytosis, hypertrophy, hyperplasia, immune cell activation, schwann cell infiltration, nerve fibrosis, macrophage infiltration, growth cone sprouting, structural integrity, sensory threshold, biochemical signaling, cell body response, dorsal root ganglia response, or a combination thereof.

In an additional method embodiment, the method can provide pain relief to a subject.

Other features and aspects of the present disclosure are discussed in greater detail below.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing and other features and aspects of the present disclosure and the manner of attaining them will become more apparent, and the disclosure itself will be better understood by reference to the following description, appended claims and accompanying drawings, where:

Figure 1A:
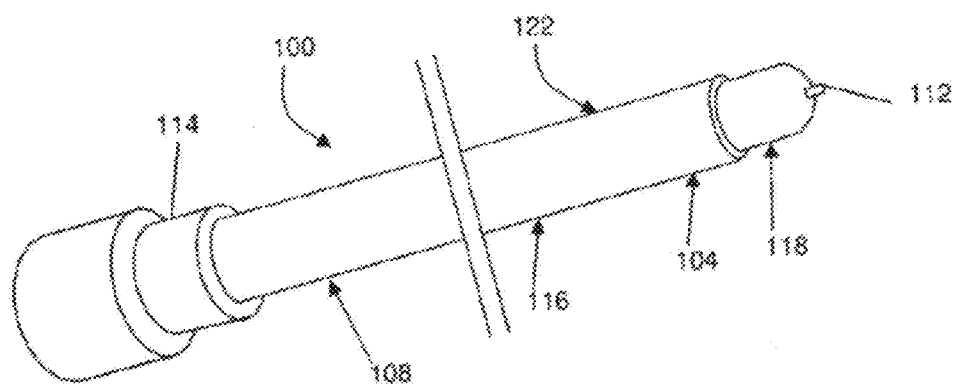
FIG. 1A is a perspective view of an embodiment of a device (e.g., percutaneous probe) that can be used in conjunction with one embodiment of the system.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Radiofrequency ablation (RFA) is a minimally invasive thermal ablation procedure commonly used to ablate multiple target sites, including the genicular nerve of patients suffering from knee osteoarthritis-induced chronic pain. However, unlike standard RFA (SRF), cooled radiofrequency ablation (CRF) provides extended pain relief that can last up to twelve months (Davis et al.). In standard radiofrequency (SRF) ablation, thermal lesions are created where the temperature is about 80° C. adjacent the probe tip and drops as the radius from the tip increases. Cooled radiofrequency (CRF) ablation overcomes the lesion size limitations inherent to SRF by circulating fluid around an approximately 60° C. probe tip to act as a heat sink by removing heat from tissue adjacent to the electrode. However, the thermal profile/physics behind a water-cooled probe enable the generation of temperatures upwards of about 80° C. surrounding the approximately 60° C. probe. This has been measured via thermal mapping. This unique thermal profile allows for CRF ablations to have larger lesion volume, for angle independence in the procedure, and a larger distal projection, all of which in turn increases the likelihood of the physician ablating the target nerve. Generally speaking, CRF can deliver greater energy with greater thermal damage, and therefore generate larger lesions (in both volume and length) compared to SRF. The lesions generated by CRF are present longer when compared to SRF because of delayed immune repair (without being wed to theory, it is hypothesized that the immune system is able to clear the smaller lesion from a SRF ablation faster, compared to a longer time to clear the larger lesion from a larger CRF ablation). The greater amount of energy and thermal damage induced by CRF causes more signaling disruption in pain-transmitting peripheral nerves, consequently improving pain-related central nervous system neuroadaptations and ultimately resulting in superior and prolonged pain relief.

Upon application of an effective dose of energy, perfuse tissue may exhibit a proximal or primary zone characterized by substantial coagulation of proteins visible to the unaided eye in the form of a lesion, where the energy is delivered in a controlled manner such that the primary zone is predetermined. This visible primary zone is conventionally associated with alteration (e.g., ablation, denervation, etc.) of the treated tissue (e.g., nerve tissue, cardiac muscle tissue, renal tissue, pulmonary tissue, connective tissue, skeletal muscle tissue, or a combination thereof) adequate to effectuate a desired outcome of a treatment procedure. In the pain relief context, for instance, the presence of a visible lesion in the primary zone can be indicative of effective denervation. For example, the primary zone characterized by a predetermined first level of tissue alteration may be associated with substantial coagulation of proteins visible to the unaided eye in the form of a physical lesion and, in some embodiments, may contain from about 75 percent up to about 100 percent (e.g., from up to about 95 percent to up to about 99 percent) coagulation of proteins. It is believed that persons of ordinary skill in the art interpret the primary zone of effective denervation as terminating where tissue exhibiting substantial coagulation of proteins is no longer visible to the unaided eye. However, it is also to be understood that, in some embodiments, the level of tissue alteration in the primary zone, as characterized by a visible lesion, may not be needed to achieve the desired outcome of the treatment procedure (e.g., effective denervation, ablation, etc.). Thus, by controlling the delivery of energy to create additional predetermined levels of tissue alteration in other predetermined zones (e.g., a secondary zone, a tertiary zone, etc.) that do not rise to the level of tissue alteration in the primary zone, the systems and methods disclosed herein can minimize unnecessary tissue damage, minimize discomfort to the patient, and minimize energy usage while still achieving the desired outcome of the treatment procedure (e.g., pain relief).

Controlling the amount of energy generated by the generator and delivered to an area of tissue can be achieved by, for example, controlling parameters within the generator itself (such as, but not limited to, the temperature, the ramp rate, ablation run times, and/or the current flow). Controlling the amount of energy generated by the generator and delivered to an area of tissue can also be achieved by, for example, controlling the amount of energy delivered at the tissue/probe interface by injecting various materials (including, but not limited to, saline or various biocompatible polymer materials). In some embodiments, feedback from the probe, for example, from a temperature sensing device, an impedance measuring means, or a pressure sensor, can be used to determine adjustments/control the amount of energy generated by the generator and to control the amount of energy delivered to the area of tissue. Methods for controlling the amount of energy are not meant to be limited to the aforementioned examples.

As such, while the inventors should not be held to any particular theory of operation, the systems and methods disclosed herein utilize the discovery that alteration to an area of perfuse tissue as a result of delivery of energy to the area of perfuse tissue (e.g., denervation, ablation, etc.) produces at least an additional secondary zone (or zones) of effective tissue alteration (e.g., denervation, ablation, etc.) that may be characterized by coagulation of proteins (e.g., collagen) that is not visible to the unaided eye. This secondary zone also contributes to the ability to effectively alter (e.g., denervate, ablate, etc.) a target area of nerve tissue and, as a result, provide pain relief to a patient. Further, in some embodiments, the predetermined level of tissue alteration in the secondary zone may be sufficient to achieve the desired outcome of the treatment procedure (e.g., effective denervation, ablation, etc.) without the need to reach the higher level of tissue alteration that may be associated with the primary zone. For example, perfuse tissue may also exhibit at least one secondary zone of tissue alteration adjacent, distal to, or enveloping the primary or proximal zone characterized by substantial coagulation of proteins (i.e., the primary zone visible to the unaided eye). The secondary zone of denervation may exhibit partial coagulation of proteins and such partial coagulation of proteins may not be visible to the unaided eye. For example, the partial coagulation of proteins may require histological examination or in vivo detection methods to determine the extent of coagulation. The secondary zone of tissue alteration may exhibit other tissue changes and by characterized by phenomena other than partial coagulation of proteins (e.g., immune cell infiltration, other changes in protein concentration and/or distribution, etc.). While the percent coagulation of proteins is used for convenience to characterize the locations of these zones, it is contemplated that other tissue changes, histological markers, molecular markers, in vivo detection methods (such as magnetic resonance imaging), or the like may be used. For instance, monitoring for biochemical changes and/or physiological responses such as changes in levels of perineurial collagen coagulation, epineurial collagen coagulation, endoneurial collagen coagulation, coagulative necrosis, vascular necrosis, axonal degeneration, inflammation, subacute histiocytosis, hypertrophy, hyperplasia, immune cell activation, schwann cell infiltration, nerve fibrosis, macrophage infiltration, growth cone sprouting, structural integrity, sensory threshold, biochemical signaling, cell body response, dorsal root ganglia response, or a combination thereof may be utilized to determine the boundaries for the primary zone, the secondary zone, or any additional zones of tissue alteration.

In an aspect in which the secondary zone of tissue alteration may be characterized by the partial coagulation of proteins such that it is not visible to the unaided eye, the secondary zone may contain, in some embodiments, from about 25 percent up to about 75 percent coagulation of proteins (or just slightly less than 75 percent coagulation of proteins). It is believed that persons of ordinary skill in the art in the past have failed to identify or recognize a secondary zone of tissue alteration that is not visible to the unaided eye that provides a sufficient level of tissue alteration to achieve the desired outcome of a treatment procedure, such as pain relief. This secondary zone of tissue alteration may vary in size depending on the type and amount of energy applied to the tissue just as the primary or proximal zone of tissue alteration may vary in size depending on the type and amount of energy applied to the tissue. The amount of time that the energy is delivered can also affect the size of the various zones of tissue alteration. For example, the secondary zone of tissue alteration may be smaller in overall area when energy is applied using a standard radiofrequency probe and/or a standard radiofrequency generator and the secondary zone of denervation may be relatively larger when energy is applied using a cooled radiofrequency probe and/or a cooled radiofrequency generator and cooling system. In any event, the present inventors have found that a secondary zone of tissue alteration may have a surface area that is from about 1.25 times to about 15 times, such as from about 1.5 times to about 12 times, such as from about 2 times to about 10 times, such as from about 3 times to about 8 times the surface area of the primary or proximal zone, whether the energy is applied using a standard radiofrequency probe and a standard radiofrequency generator or a cooled radiofrequency probe and/or a cooled radiofrequency generator and cooling system. Because the secondary zone increases the area of effective tissue alteration significantly, less energy can initially be applied, for instance, to ablate a targeted area of tissue since the area of effective tissue alteration extends beyond what is visible to the unaided eye.

Generally, in clinical settings, accounting for the lesioning that occurs in the secondary zone in determining the total area of tissue alteration in humans can result in a significant increase in the total area of tissue alteration, especially when cooled radiofrequency energy is applied. For instance, if the "conventional" lesion is a sphere having a diameter of about 10 millimeter (mm) and thus a radius of about 5 mm, where the conventional lesion is referred to as the primary zone of effective tissue alteration (e.g., denervation, ablation, etc.), and it is enveloped by a generally spherical concentric intermediate lesion that may not be visible to the unaided eye and that is referred to as the secondary zone of effective tissue alteration) that has a thickness/radius of about 5 mm to about 10 mm on each side of the "conventional" lesion, the area of effective tissue alteration will increase by a factor of about 3 when the secondary zone has a thickness of about 5 mm up to a factor of about 8 when the secondary zone has a thickness of about 10 mm. This is based on the difference between the area of a sphere approximating the primary zone of effective tissue alteration having a radius of 5 mm (spherical surface area of 314.16 mm$^2$) and the area of the concentric sphere approximating the secondary zone of effective tissue alteration having a radius of from 10 mm (spherical surface area of 1256.64 mm$^2$) to 15 mm (spherical surface area of 2827.43 mm$^2$). The factor differences are calculated as (1256.64 mm$^2$-314.16 mm$^2$)/314.16 mm$^2$=3 and (2827.43 mm$^2$-314.16 mm$^2$)/314.16 mm$^2$=8.

These increases are similar for standard radiofrequency ablation. For example, a sphere approximating the primary zone of effective tissue alteration having a radius of about 2.5 mm (spherical surface area of 78.54 mm$^2$) and a concentric sphere approximating the secondary zone of effective tissue alteration having a radius of from about 5 mm (spherical surface area=314.16 mm$^2$) to about 7.5 mm (spherical surface area=706.86 mm$^2$) will result in an increase in the area of effective tissue alteration by a factor of about 3 (at a radius of about 5 mm) up to a factor of about 8 (at a radius of about 7.5 mm).

In addition to contemplating a system and method for controlling energy delivered to an area of tissue to form a predetermined primary zone of tissue alteration and/or a predetermined secondary zone of tissue alteration as evidenced by varying degrees of protein coagulation and the presence of a visible lesion in the primary zone and the absence of a visible lesion in the secondary zone, the systems and methods disclosed herein contemplate controlling the energy delivered to the area of tissue to form a predetermined tertiary zone of tissue alteration. The tertiary zone can exhibit a predetermined level of tissue alteration that is characterized by a lesser extent of tissue damage than the primary zone and the secondary zone. For example, in some embodiments, the tertiary zone of tissue alteration may be characterized by less than 25 percent coagulation of proteins (but greater than 0 percent coagulation of proteins). The level of tissue alteration in the tertiary zone can be controlled by the energy delivered to the area of tissue to be treated. Further, the energy delivered to the area of tissue can be determined by studying and analyzing the biochemical changes and/or physiological responses that result from different levels of energy being delivered to the tissue. Such biochemical changes and/or physiological responses include perineurial collagen coagulation, epineurial collagen coagulation, endoneurial collagen coagulation, coagulative necrosis, vascular necrosis, axonal degeneration, inflammation, subacute histiocytosis, hypertrophy, hyperplasia, immune cell activation, schwann cell infiltration, nerve fibrosis, macrophage infiltration, growth cone sprouting, structural integrity, sensory threshold, biochemical signaling, cell body response, dorsal root ganglia response, or a combination thereof. Further, it is to be understood that in some embodiments, altering the tissue to a lesser extent in the tertiary zone may be sufficient to effectuate the desired outcome (e.g., pain relief) without having to form the primary zone and/or secondary zone of tissue alteration, which can help minimize unnecessary tissue damage, minimize discomfort to the patient, and minimize energy usage while still achieving the desired outcome of the treatment procedure (e.g., pain relief).

Moreover, it is to be understood that the coverage area (e.g., the area of tissue alteration) and the level or extent of tissue alteration associated with the primary zone, the secondary zone, the tertiary zone, or a combination thereof can be determined via a relationship between the amount of energy delivered to the area of tissue, an amount of time during which the energy is delivered, a waveform type (e.g. pulsed or continuous, high frequency or low frequency, high amplitude or low amplitude, etc.), device placement, device location, device dimensions, surgical approach, a temperature at which the energy is delivered, or a combination thereof. The coverage area of the zone can, in some embodiments, be predetermined using a variety of imaging modalities, including, but not limited to, fluoroscopic (live X-ray), ultrasound, or MRI.

Figure 1B:
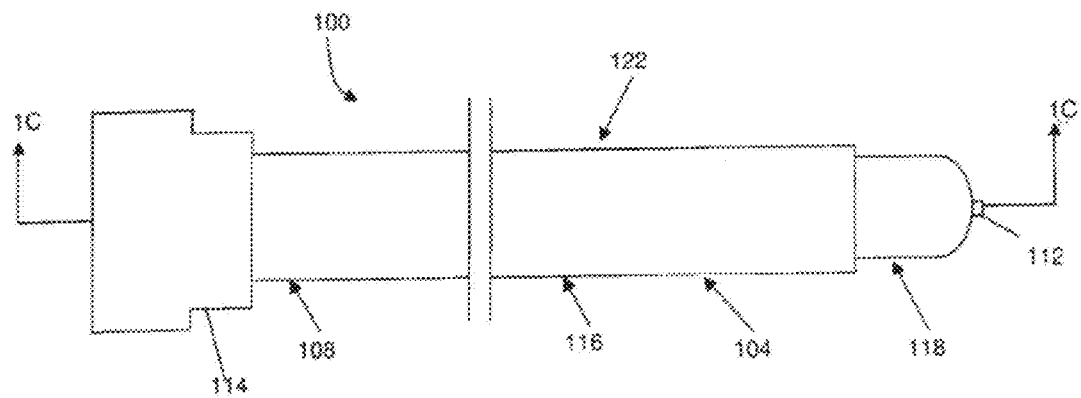
FIG. 1B is a top view of the embodiment of FIG. 1A.
Figure 1C:
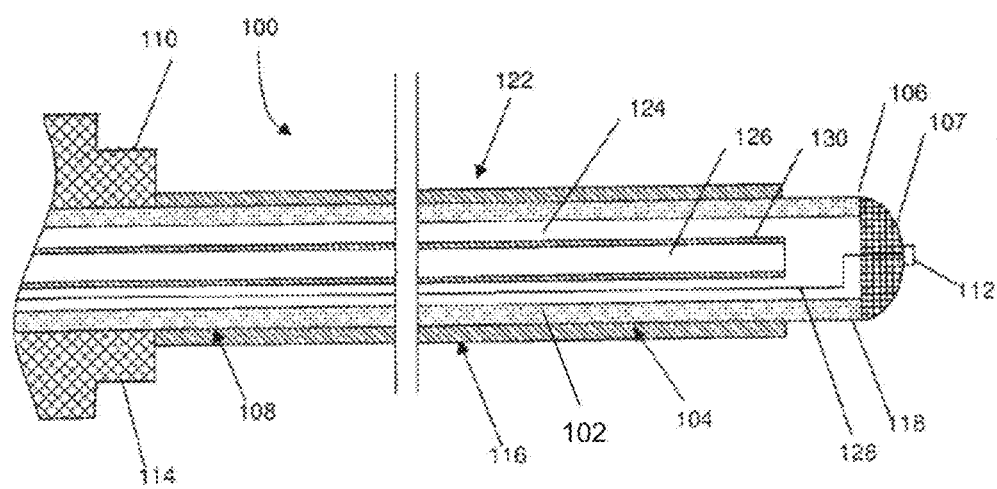
FIG. 1C is a cross-sectional view of the embodiment of FIG. 1A taken along the line 1C-1C in FIG. 1B.
Figure 2A:
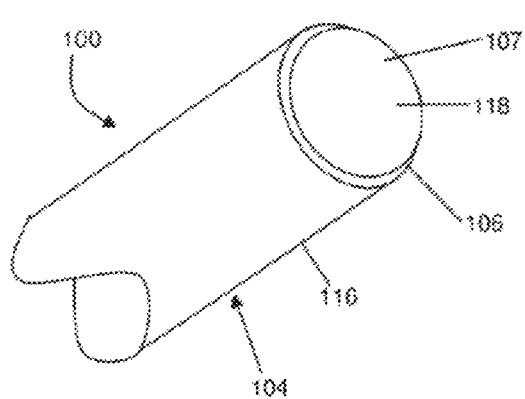
FIGS. 2A to 2D are perspective views showing configurations of electrically insulated portions and electrically exposed conductive portions (i.e., active electrode portions) of several embodiments of a device (e.g., percutaneous probe) that can be used in conjunction with the system.
Figure 2B:
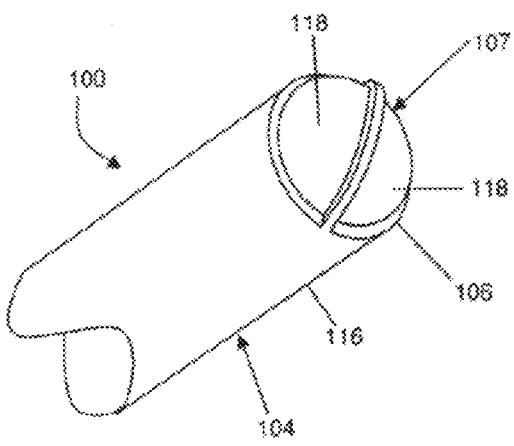
Figure 2C:
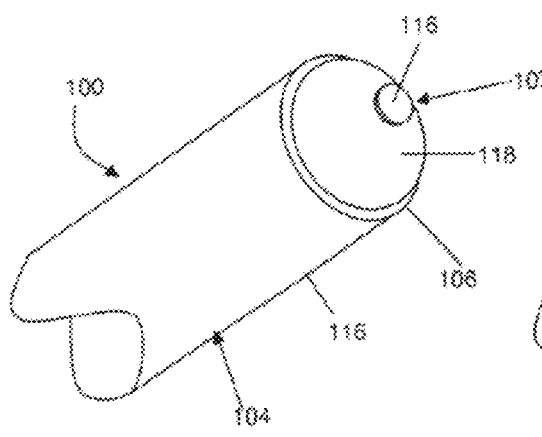
Figure 2D:
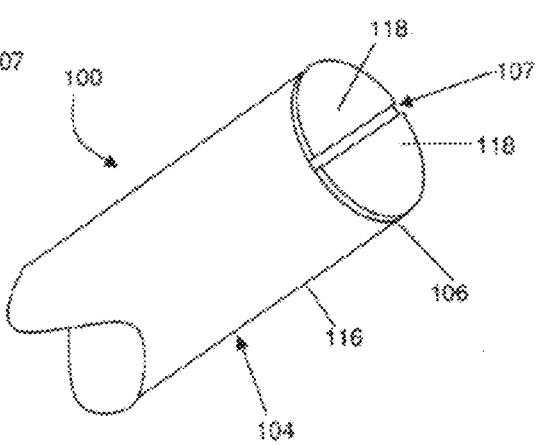

Referring now to the drawings, and beginning with FIGS. 1A to 1C, various features of the systems and methods are discussed in more detail. As shown, the device for applying radiofrequency energy to an area of tissue to be altered during a treatment procedure, such as a denervation or ablation procedure, may be a probe 100, such as a percutaneous probe; however, in other embodiments, the device may be a cannula, a catheter, or any other elongate member capable of delivering energy to a target tissue site within a patient's body. For the sake of clarity, the term "probe" is used throughout the specification to describe any such component. The probe 100 may be an elongate member that can include a shaft 122, a distal region 104, a distal end 106, a distal face 107, a proximal region 108, and a proximal end 110. As used herein, the terms "distal" and "proximal" are defined with respect to the user and when the device is in use. That is, the term "distal" refers to the part or portion further away from the user and closest to the treatment site, while the term "proximal" refers to the part or portion closer to the user and farthest from the treatment site when the device is in use.

In some embodiments, the probe 100 may define at least one lumen 124, as will be described in more detail below. Furthermore, in some embodiments, either or both of the distal end 106 and the proximal end 110 may define at least one aperture, which may be in communication with the lumen 124.

As shown in the embodiments contemplated by FIGS. 1A to 1C, the probe 100 can be formed of a conductive material 102, where the probe 100 can have an electrically insulated portion 116 where the conductive material 102 is covered with an insulating material and an electrically exposed conductive portion 118 where the conductive material 102 is exposed. The electrically exposed conductive portion 118 can also be referred to as an active electrode, and when the exposed conductive portion is located at the distal end of probe 100, it may be referred to as an active tip. In general, the electrically insulated portion 116 may extend from the proximal region 108 of the probe 100 to a location in the distal region 104 of the probe 100. The location to which electrically insulated portion 116 extends may depend on the application, as will be discussed in more detail below. Furthermore, the location to which electrically insulated portion 116 extends may not be fixed. In other embodiments, as shown in FIGS. 2A to 2D, the probe 100 can include more than one electrically insulated portion 116 and/or more than one electrically exposed conductive portion 118.

Figure 5A:
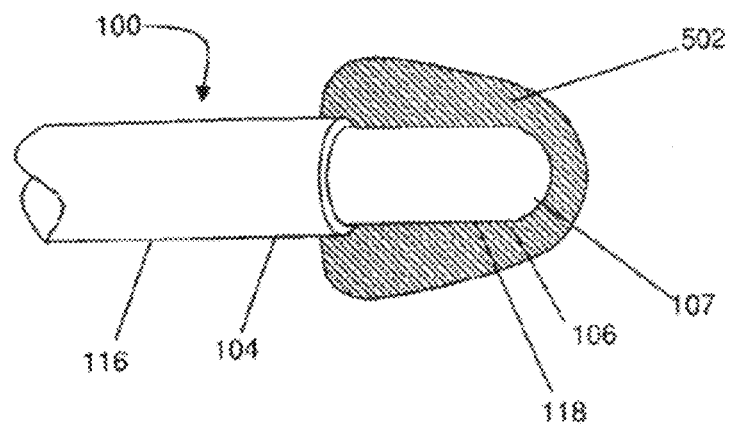
FIGS. 5A to 5D are partial perspective views showing embodiments of a distal region of a probe that can be used in the system and examples of lesions formed therefrom.
Figure 5B:
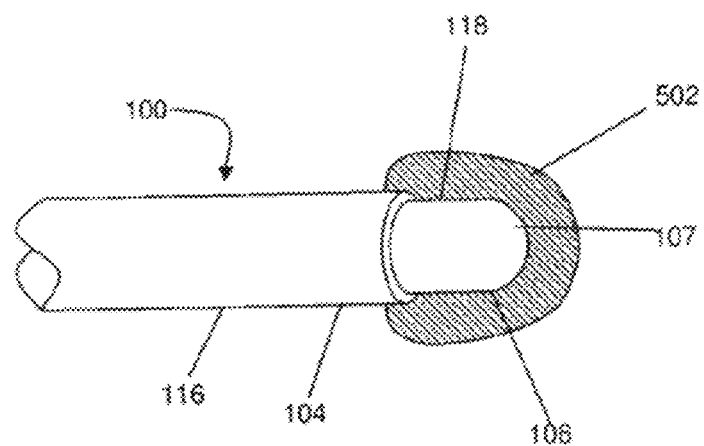
Figure 5C:
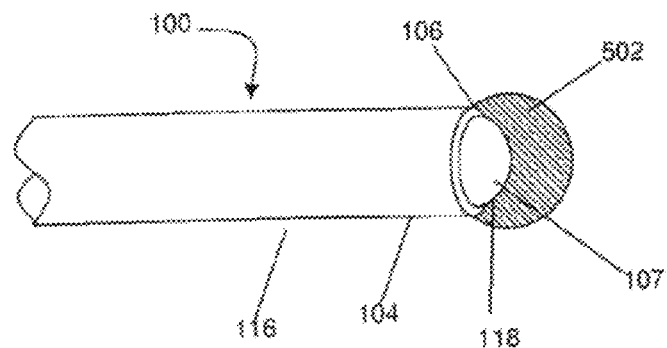
Figure 5D:
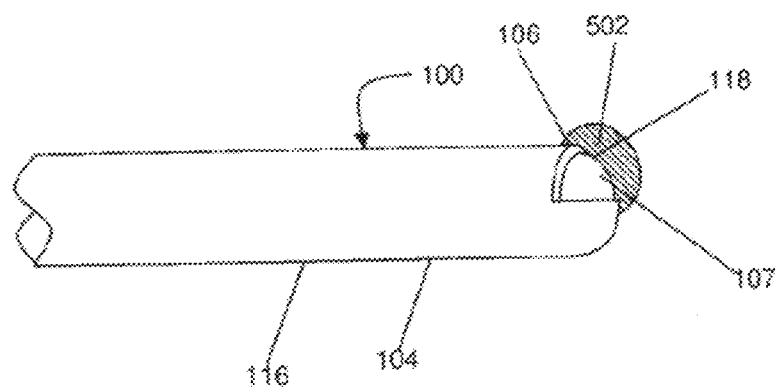
Figure 6:
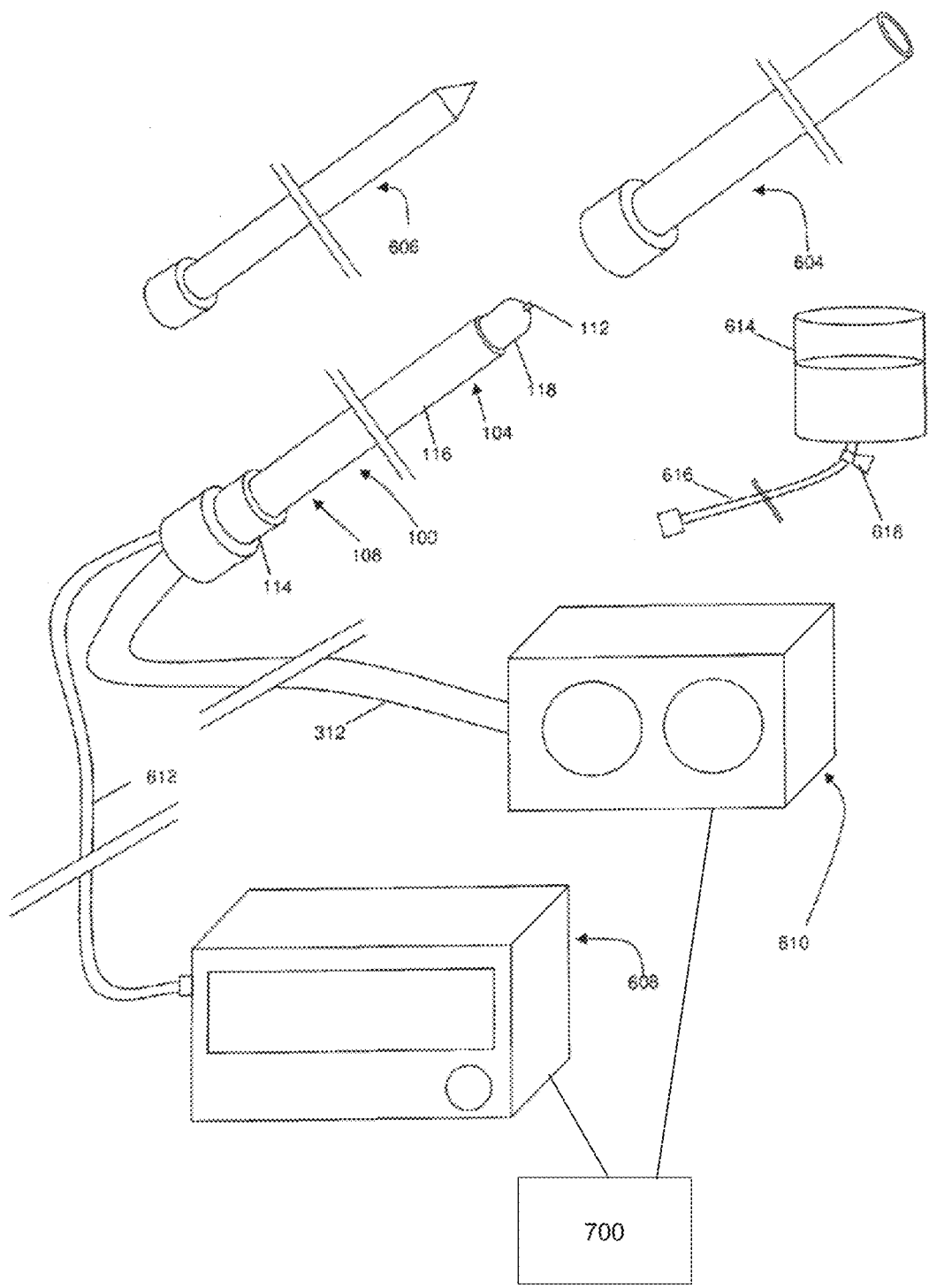
FIG. 6 is a perspective view of an embodiment of a system.

In some embodiments, for example as shown in FIG. 1A to 10, the proximal region 108 of the probe 100 can include a hub 114. The hub 114 may be structured to securely connect other devices such as introducers, connector cables, cannulae, tubes, or other hubs, for example, to the probe 100. For example, as shown in FIG. 6 and discussed in further detail below, the probe 100 may be coupled to an energy generator and/or to a source of cooling via respective connecting means (for example, an electrical cable and/or flexible tubing) which may be associated with the hub 114 (also shown in FIG. 3). The hub 114 may also serve as a handle or grip for the probe 100 and can serve as a locking mechanism to secure the probe 100 to an introducer 604. The hub 114 may be manufactured from a number of different materials, including, but not limited to, plastics, polymers, metals, or combinations thereof. Furthermore, the hub 114 may be attached to probe 100 by a number of different means. For example, in one embodiment, the hub 114 may be made from polypropylene, and may be attached to probe 100 by any suitable fitting such as a luer fitting. Although the hub 114 can serve as a handle, it is also to be understood that a separate handle 120 is also contemplated in which cooling tubes 310 and 312 can be located and which are discussed in more detail below.

The size and shape of the probe 100 may vary depending on the application, and the invention is not limited in this regard. For example, in some embodiments, the transverse cross sectional shape of the probe 100 may be substantially circular. In other embodiments, the cross-sectional shape may be substantially polygonal, elliptical, or any other desired shape. In some embodiments, the length from the distal end 106 to proximal end 110 of the probe 100 may be between about 5 centimeters (cm) and about 40 cm and the outer diameter of shaft 122 may be between about 0.65 millimeters (mm) and about 2.00 mm (between about 20 AWG and about 12 AWG). In one specific example, the length of the probe may be about 7.5 cm, the outer diameter may be about 1.5 mm, and the transverse cross-sectional shape may be substantially circular. Further, it is to be understood that the shape of the distal end 106 may vary depending on the application. Possible shapes include, but are not limited to, blunt, rounded, sharp, and beveled.

The probe 100 may be rigid or flexible and may be straight, bent or angled at one or more points along its length. As used herein, the term "bent" refers to any region of non-linearity or any deviation from a longitudinal axis, gradual or abrupt, and at any angle. In embodiments wherein the probe 100 is bent, the bend may be at various locations along the probe 100, for example in the distal region 104. Furthermore, the bend may be of a variety of degrees and lengths. For example, the bend may traverse about 25° of a circle, and occur over a length of about 5 mm. In addition, the probe 100 can include a plurality of bends, which may or may not be in the same plane. For example, in some embodiments, the probe 100 may be bent such that it is helical or "corkscrew" shaped. In some embodiments, the probe 100 may be structured such that its shape may be modified by a user before or during the course of a procedure. More specifically, the shape of the distal region 104, for example, may be modified such that it may change from a straight to a bent configuration using an actuating mechanism. This may aid in accessing difficult to reach sites within the body and can be accomplished by a variety of means. For example, the probe 100 can include at least one active shape control mechanism, including but not limited to one or more pull-wires, a hydraulic or piezoelectric device, or another actuating mechanism.

In one embodiment, the electrically insulated portion 116 may be formed by coating a conductive portion 102 of the shaft 122 with an electrically insulative coating, covering, or sheathing. In other words, the probe 100 can include electrically insulative material disposed on the surface of the elongate member. For example, in one embodiment, the shaft 122 of the probe 100 may be fabricated from a biocompatible metal or alloy, for example stainless steel, which may be overlaid in part by an insulating coating, for example polytetrafluoroethylene (PTFE). In other embodiments, the shaft 122 can be fabricated from another metal, such as nitinol or titanium, and/or another electrically insulating material, including but not limited to polyethylene terephthalate (PET), may be disposed thereon. In other embodiments, other metals or electrically insulating materials may be used, and the invention is not limited in this regard. Furthermore, the insulating material may be semi-porous, to allow for some leakage of current through the insulating material. In some embodiments, the material may also be a thermal insulator as well. In still other embodiments, different insulating materials can be used for different portions of the probe 100. The insulating coating may be applied to a portion of shaft 122 by dip-coating, spraying or heat shrinking, for example. Meanwhile, the remaining uncoated portion of the distal region of the shaft 122 may serve as a conductive portion 118.

In another embodiment, the shaft 122 of the probe 100 can be fabricated from an insulative or non-conductive material and may be furnished with one or more externally applied electrodes 118. In such embodiments, the probe 100 can include one or more wires that may be attached to the electrode(s) 118 at one end, and can run proximally along the shaft 122, such that a proximal portion of the wire(s) may be operatively connected to an energy source, thereby supplying energy to the electrodes 118. For example, the shaft 122 can be fabricated from Radel™ plastic, and the externally applied electrodes can be fabricated from stainless steel.

In alternate embodiments, the shaft 122 may be manufactured from a combination of materials. For example, the distal region 104 of the shaft 122 can be made from a material such as nitinol, such that the shape of the distal region 104 may be altered, and the remainder of shaft 122 may be made from stainless steel, such that the remainder of shaft 122 may be substantially fixed.

In some embodiments, the probe 100 may be cooled. In some specific embodiments, the probe 100 may be cooled by the internal circulation of a cooling fluid. Such a configuration, whereby a cooling medium does not exit from a distal region 104 of the probe 100, may be referred to as an internally-cooled probe. The cooling fluid may be any fluid suitable for removing heat from probe 100 during surgery, such as water. Other examples of cooling fluid include, but are not limited to, liquid nitrogen and saline. Furthermore, the cooling fluid may be at any temperature suitable for removing heat from the probe during surgery, for example between about 0° C. and about 25° C. More specifically, the temperature of the fluid may be at about room temperature (21° C.), about 4° C., or about 0° C., depending on the application.

In addition, the cooling fluid may be delivered or circulated at a wide range of flow-rates, and the invention is not limited in this regard. An appropriate flow-rate may be determined or calculated based on a number of factors, including the conductivity and heat capacity of the probe 100, the cooling fluid and/or the tissue, the internal structure of the probe 100, and the desired temperature of the distal end 106 of the probe 100, among other factors. In some embodiments, the cooling fluid may be delivered at flow ranging from about 10 milliliters/minute (ml/min) to about 30 ml/min.

Figure 3A:
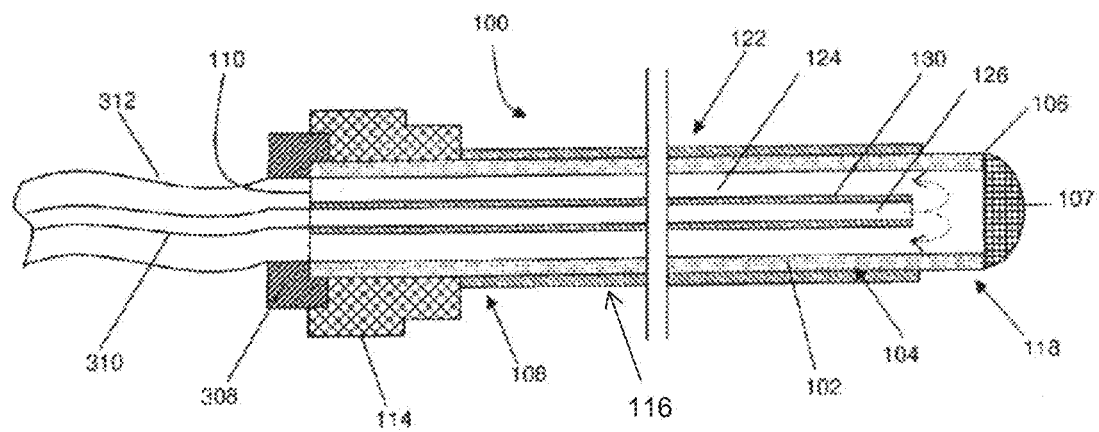
FIGS. 3A to 3E are cross sectional views of several embodiments of devices (e.g., percutaneous probes) that can be used in the system.
Figure 3B:
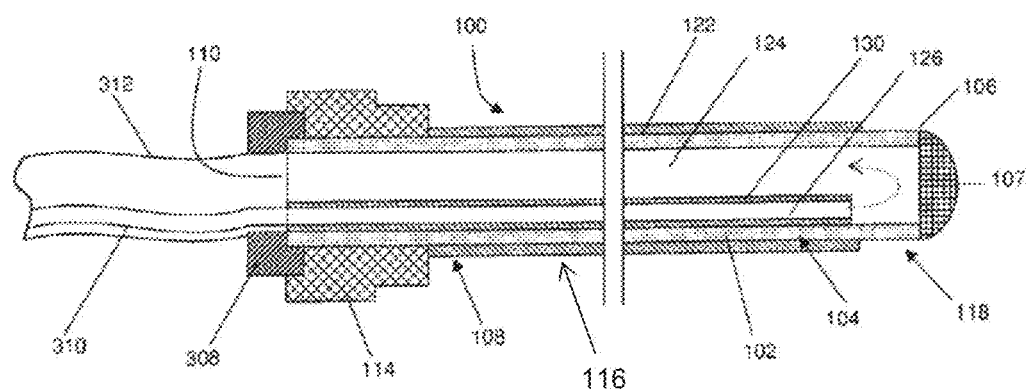
Figure 3C:
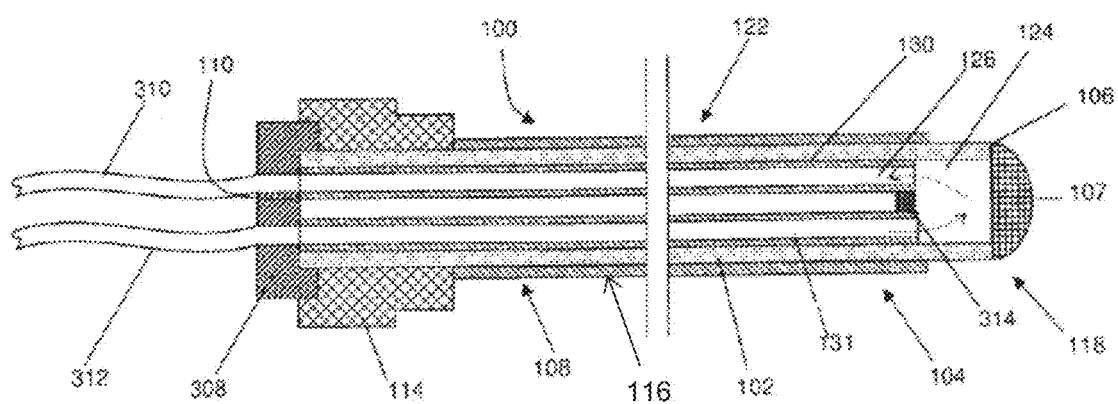
Figure 3D:
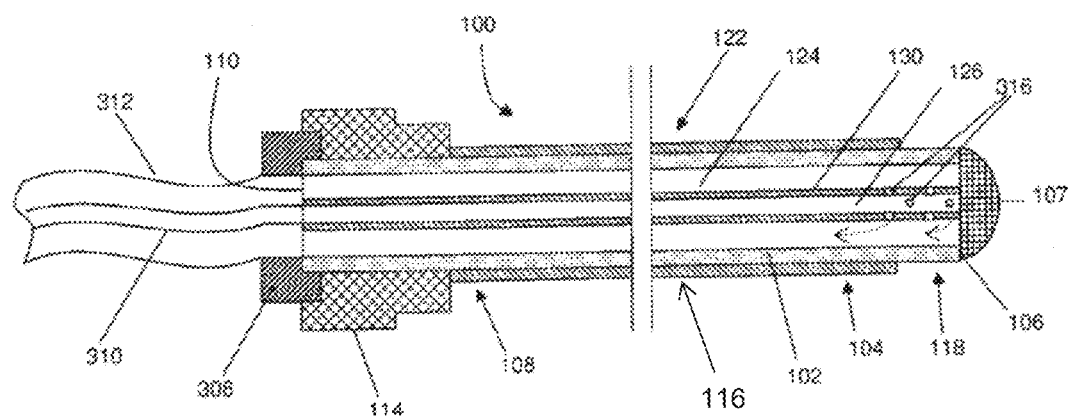

Several embodiments of the internal structure of a probe 100 cooled by the internal circulation of a cooling fluid are shown in FIGS. 3A to 3C. As shown in FIG. 3A, the shaft 122 of the probe 100 may define a first lumen 124, and the proximal end 110 of the probe 100 may be open and in communication with lumen 124. Meanwhile, the distal end 106 of the probe 100 may be closed. The probe 100 may further include an internal tube, cylinder, or cannula 130 disposed within the lumen 124 that defines a second lumen 126. The internal tube 130 may have an open distal end, which may be located proximally to distal end 106 of probe 100, and an open proximal end. The proximal end of internal tube 130 may be structured to be operatively connected to a source of cooling fluid. For example, the probe 100 can include a hub 308, which may connect internal tube 130 to a flexible tube 310. In an alternate embodiment, the hub 114 may be structured to connect internal tube 130 to flexible tube 310, such that the hub 308 is not required. Embodiments including the hub 308, however, may be beneficial in that the hub 308 may allow for tubing 310 to be removable. The proximal end of the tube 310 may be connected to the cooling source, for example a reservoir of fluid, whereby the tube 310 functions as an inflow tube for cooling fluid from the reservoir to the probe 100. That is, the tube 310 may function to deliver fluid to the distal region of probe 100. Thus, in use, cooling fluid may flow from the reservoir of fluid, through the inflow tube 310, and into the internal tubing 130. The fluid may subsequently exit the distal end of the internal tubing 130, flow into the lumen 124 of the probe 100, and exit the probe 100 via the open proximal end 110. The open proximal end 110 may be coupled to means for returning the fluid to the reservoir. For example, another flexible tube 312 may operatively connect the proximal end 110 to the reservoir, such that the tube 312 functions as an outflow tube for the cooling fluid. In the embodiment shown in FIG. 3A, the first and second lumens 124 and 126 are coaxial; however, in other embodiments, the second lumen 126 may not be centered about the longitudinal axis of the probe 100, as shown in FIG. 3B. In an alternate embodiment, as shown in FIG. 3D, the internal tube 130 can include one or more apertures 316, from which fluid may exit the internal tube 130 and enter the lumen 124 of the probe 100. In this embodiment, the internal tube 130 may extend to the distal end 106 of the probe 100. In another embodiment, fluid may enter the probe 100 via the open proximal end 110, and exit the probe 100 via the tube 130. That is, the inflow tube 310 may function to remove fluid from the distal region of the probe 100. Tubing 310 and 312 may be made from a variety of materials. For example, tubing 310 and 312 can be fabricated from a flexible plastic material, such as Tygon™, polyvinylchloride (PVC) or polycarbonate. In some embodiments, tubing 310 and 312 can include markings or other means of identification, such that the inflow tubing is distinguishable from the outflow tubing. In alternate embodiments, fluid exiting the probe 100 may not be returned to the source of cooling, but may rather be removed to another location, for collection and/or disposal of the fluid.

Figure 3E:
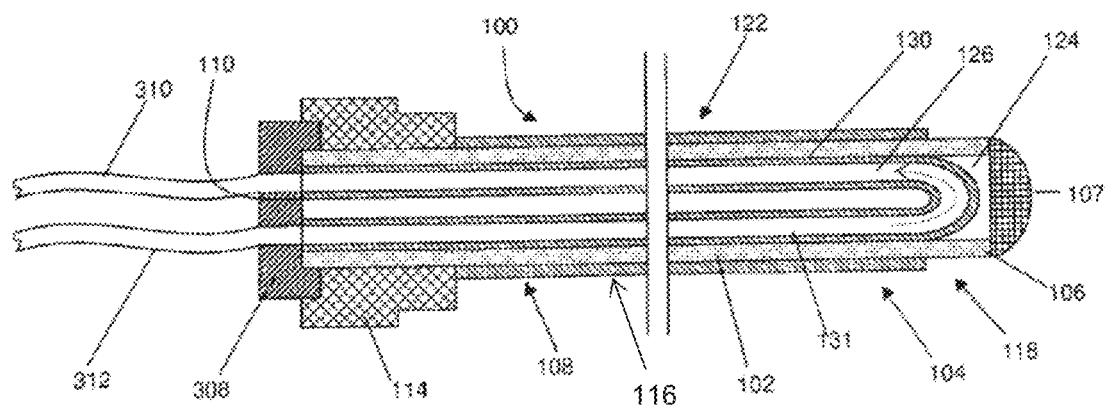

In another embodiment, as shown in FIG. 3C, the probe 100 can include a plurality of inner tubes for the circulation of cooling fluid. For example, the probe 100 can include first and second internal tubes 130, 131. Each internal tube 130, 131 can have an open distal end, which may lie proximally to the distal end 106 of the probe 100, and an open proximal end. The first internal tube 130 can deliver a cooling fluid from a reservoir to the distal region of probe 100. The cooling fluid may then return to the reservoir via the second tube 131. As described hereinabove, flexible inflow and outflow tubes 310 and 312 can be provided, which may operatively connect internal tubes 130, 131, to a reservoir of fluid or other source of cooling fluid. In an alternate embodiment, as shown in FIG. 3E, the probe 100 can include a single inner tube 131, which may be substantially U-shaped, such that the cooling fluid enters and exits the probe 100 from opposite ends of the tube 131. In other embodiments, various quantities, orientations and/or configurations of the internal tubes can be provided within the probe 100 as known to one of ordinary skill in the art.

In embodiments wherein the probe 100 is bent, as described hereinabove, the internal tubes 130 and/or 131 may be structured to accommodate the bend. For example, in one embodiment, the internal tubes 130 and/or 131 may be bent at a similar location and angle as the probe 100. In another embodiment, the internal tubes 130 and/or 131 may end at a location that is proximal to the location where the probe 100 bends. In embodiments wherein the shape of the probe 100 is structured to be modified before or during a procedure, the internal tubes 130 and/or 131 may be structured such that their shape is also modified along with the probe 100.

In some embodiments, a flow impeding structure or plug 314 can be used to restrict the flow of cooling fluid within the probe 100. For example, in the embodiment shown in FIG. 3C, a plug 314 may optionally be used to fill a portion of the lumen 124 such that any cooling fluid supplied to the probe 100 that is not located within one of the internal tubes 130 or 131 is confined to a distal region 104 of the probe 100. In other words, cooling fluid may flow from a reservoir, through the first internal tube 130, to the distal region 104 of the probe 100. The cooling fluid may then circulate within the portion of the lumen 124 that is distal to the plug 314 in order to provide cooling to the distal region 104 of the probe 100. The cooling fluid may then exit the probe 100 through the second internal tube 131 and return to the reservoir. In some embodiments, the plug 314 may be made of a radiopaque material, for example silver solder, such that the plug 314 may also function as a radiopaque marker when visualized using fluoroscopic or fluorographic imaging. In alternate embodiments, other materials may be used for the lug 314 instead of silver solder, and the invention is not limited in this regard.

Means for cooling the probe 100 may include, but are not limited to, circulation of a cooling fluid, for example as described above, cooling by a thermoelectric circuit, or chemical cooling by an endothermic reaction. In some embodiments, the probe 100 may be cooled by a thermoelectric circuit. For example, the probe 100 may partially or fully house a circuit comprising two dissimilar metals or semiconductors, for example P- and N-doped bismuth-telluride, which are joined together at two junctions. When current passes through the circuit, heat may be transferred from one junction to the other. This phenomenon is known as the Peltier Effect. The junction where the heat is transferred from may be located in the distal region of the probe 100, and the junction where the heat is transferred to may be located at a proximal region of the probe 100 or externally to the probe 100. Energy may be provided to the circuit by an external energy source (for example, the same energy source that delivers RF energy to the probe 100), an electrical generator or a battery, for example.

In an alternate embodiment, the probe 100 may be cooled chemically. For example, the probe 100 can include two internal tubes, similar to the structure shown in FIG. 3C. The proximal end of the tubes may each be operatively connected to a separate reservoir of material. The distal end of each tube may deliver material from each respective reservoir to the distal region 104 of the probe 100. The materials in the separate reservoirs may be selected such that when mixed, an endothermic reaction or endothermic mixing occurs. Thus, when each material exits its respective internal tube and reaches the distal region of the probe 100, the materials will mix, thermal energy will be absorbed, and the distal region 104 of the probe 100 will be cooled. The product(s) of the endothermic reaction or the resulting mixture may exit the probe 100 via the open proximal end 110. One example of a suitable reaction for the chemical cooling of the probe 100 may be the mixing of water and tetrahydrofuran, however because of the toxicity of chemicals of this nature, suitable precautions may have to be taken to ensure no leakage during use.

Referring now to FIG. 6, one or more cooling fluids may be delivered from a reservoir to the lumen 124 of the probe 100 for the purposes of cooling the probe 100. The fluid(s) may be delivered to the probe via a number of means, and the invention is not limited in this regard. For example, in one embodiment, the reservoir of fluid can include a container, for example an intravenous (IV) bag 614, which is elevated above the patient. The tubing 616, which can be any suitable clear plastic flexible tubing, can be used to connect the reservoir to an inlet in the probe 100. A valve 618 can be placed at the junction of the container/bag 614 and the tubing 616 (or at some other location between the container and the probe), such that when the valve is opened, gravity may cause fluid to flow towards the probe 100. After circulation within the probe 100, fluid may exit the probe 100 via tubing 616 similar to tubing 312, which may drain into another reservoir, for example a second IV bag. In another embodiment, at least one pump may be used to deliver fluid to the probe 100. For example, at least one peristaltic pump 610 can be operatively connected to a reservoir of fluid. The reservoir of fluid may be an IV bag, a polypropylene vial or burette, or another container, for example. The pump(s) may pump the fluid from the reservoir to an inlet in the probe 100. After circulating in the probe 100, the fluid may exit the probe 100 through an outlet in probe 100 and may flow through a tube to either the same or a different reservoir or, alternatively, to an alternate location as described above. A second pump, gravity, or a source of suction, for example, may assist in drawing the fluid out of the probe.

In some embodiments, the probe 100 can be sterilizable. In these embodiments, the tubing 310 and 312 may or may not be sterilizable as well. The probe 100 can be sterilized by, for example, steam, ethylene oxide, or radiation sterilization without risk of material degradation or discoloration. In order for the probe 100 to be sterilizable, the probe 100 can be made from sterilizable materials. For instance, the conductive portion 102 of the shaft 122 can be made from stainless steel and the electrically insulative coating 116 may be made from PTFE. In embodiments where the tubing 310 and 312 are sterilizable, tubing 310 and 312 can be made from medical/surgical Tygon tubing. In other embodiments, tubing 310 and 312 can be detachable from probe 100, and therefore may not be required to be sterilizable. In this embodiment, the probe 100 can include at least one connector, which may be sterilizable, for connecting the probe 100 to the tubing 310 and 312, or another fluid source. The at least one connector can include means for securing a fluid source to the probe 100 such as a luer lock, which may fit between tubing 310 and 312 and lumen 124, thus allowing for fluid communication between the tubing 310 and 312 and the lumen 124. In one embodiment, the probe 100 can include two sterilizable connectors, one of which may couple a tube for inflowing fluid to one of the lumen 124 and the internal tube 130, and the other of which may couple a tube for outflowing fluid to the other of the lumen 124 and the internal tube 130.

Figure 4A:
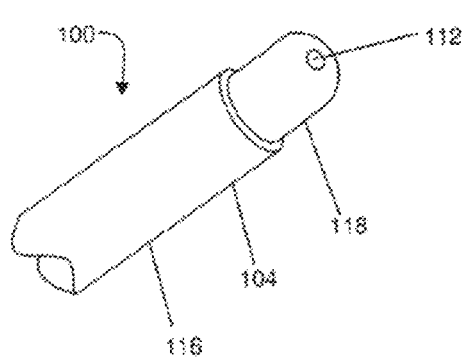
FIGS. 4A to 4C are partial perspective views showing configurations of temperature measuring devices that can be used in several embodiments.
Figure 4B:
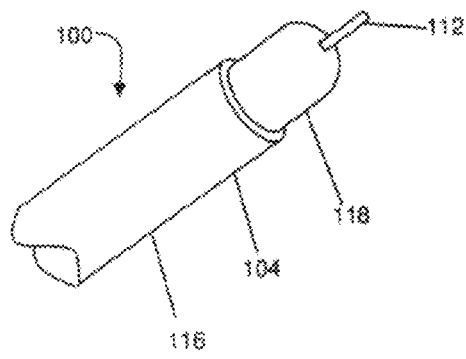
Figure 4C:
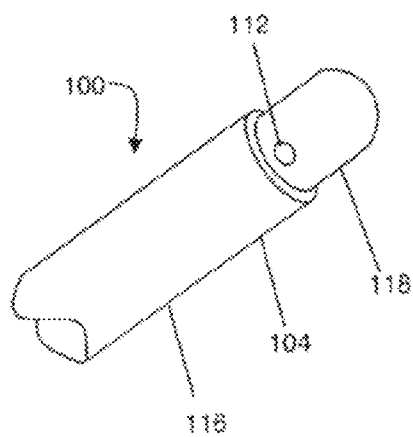

In some embodiments, the probe 100 can include at least one temperature sensing device 112 (i.e., a temperature sensor). The temperature sensing device 112 can be any means for sensing and/or measuring temperature, including, but not limited to, a thermocouple, a thermistor, an optical fluorescence sensor, or a resistance thermometer. In some embodiments, the temperature sensing device 112 can be positioned at the distal region 104 of the probe 100, for example at distal end 106. As shown in the embodiments of FIGS. 4A to 4C, the temperature sensing device 112 can have various configurations. For example, as shown in FIG. 4A, the temperature sensing device 112 can be disposed at the distal end 106 and can be substantially flush with the distal end 106. In another embodiment, as shown in FIG. 4B, the temperature sensing device 112 can protrude from the distal end 106, such that it may measure the temperature of a material that is located distal to distal end 106, rather than the temperature of the probe 100 itself or of material adjacent to the probe 100. In another embodiment, as shown in FIG. 4C, the temperature sensing device 112 can be located proximally to the distal end 106. In further embodiments, the probe 100 can include additional temperature sensing devices. For example, a first temperature sensing device may be located at the distal end 106 of the probe 100, and a second temperature sensing device may be located distal to the distal end 106 of the probe 100, such that the temperature at the distal end 106 of the probe 100 as well as in the tissue may be measured. In other embodiments, other configurations are possible, and the invention is not limited in this regard. Furthermore, in the embodiments shown in FIGS. 4A and 4C, the temperature sensing device may be located within the probe 100, or on the external surface of the probe 100.

In an alternate embodiment, the temperature sensing device 112 can be located within the lumen 124 of the probe 100 so as to measure the temperature of a cooling fluid. By monitoring the change in temperature of the cooling fluid, which relates to the amount of heat being drawn away from the probe 100, the temperature of the tissue located adjacent conductive portion 118 can be determined.

In another embodiment, the probe 100 can include an extendible remote temperature sensing element which may be deployed from the probe 100. An extendible temperature sensing device 112 may allow monitoring of the temperature within tissues located remotely from the surface of the conductive portion 118. The extendible temperature sensing device 112 may further be steerable so that its position may be changed during a procedure to obtain temperature measurements from a variety of tissue regions.

In some embodiments, the probe 100 can include means for operatively connecting the temperature sensing device 112 to an external device. For example, such a device can be a display or screen, such that the temperature measured by the temperature sensing device may be viewed by a user. In other embodiments, the external device can be an electrical generator, such that temperature feedback can be provided to the electrical generator. Means for operatively connecting the temperature sensing device 112 to an external device can include an insulated wire 128, which can extend proximally from the temperature sensing device 112, through a lumen of the probe 100, and out of the probe 100 through its proximal end 110. The wire 128 can be any temperature or electrical conductor capable of operatively connecting the temperature sensing device 112 to an external device. Alternatively, the temperature sensing device 112 can be operatively connected to an external device via a wireless connecting means, including, for example, infrared or Bluetooth™. Further details regarding temperature sensing devices can be found in U.S. Patent Application Publication No. 2005/0177209 to Leung, et al., which is incorporated herein by reference.

In some embodiments, the probe 100 can include a sensor for measuring impedance. As the impedance of a tissue may be a characterizing factor, measuring the impedance of tissue proximal to the probe 100 can help confirm placement within a desired tissue type. In some embodiments, the probe 100 can be structured to measure the electrical impedance between, for example, two points on the probe 100 or between a point on the conductive portion 118 and a point on an auxiliary device such as a cannula or a grounding pad. Further details regarding impedance measuring means may be found in U.S. Patent Application Publication 2005/0177209 to Leung, et al., which is incorporated herein by reference. In some embodiments, the probe 100 can include a sensor for measuring pressure. The means of measuring pressure can include a lumen in fluid communication with fluid in a patient's body as well as with a pressure transducer to record the pressure measurements. In other embodiments, the pressure sensor can include a pressure transducer disposed at a desired location on the probe 100.

As mentioned above with respect to the temperature sensing device, the probe 100 can include means for operatively connecting any impedance or pressure measuring means to an external device. For example, a pressure transducer may be electrically coupled to a wire located within the probe 100, which wire maybe further electrically coupled to an external device to transmit a signal from the pressure transducer to the external device.

In some embodiments, probe 100 can include means for enhancing the visualization thereof, for example when viewed under fluoroscopic imaging or another imaging modality. Such means may be a visible marker, a radiopaque marker or markers for use with magnetic resonance imaging or ultrasound, for example. Further details regarding enhanced visualization are disclosed in U.S. Pat. No. 7,593,778 to Chandran, et al. and U.S. Patent Application Publication 2004/0176759 to Krishnamurthy, et al., both of which are incorporated herein by reference.

In some embodiments, the hub 114 can have markings to indicate, for example, the direction/orientation of a bend or curve of the probe 100 or the location of an aperture or a temperature or pressure sensing device on or within the probe 100. These markings may be visual indicators, or tactile indicators, which may be textured or raised so that the user may see or feel the markings while manipulating the probe 100.

In some embodiments, the probe 100 can be furnished with at least one aperture, which may be in fluid communication with the lumen 124. Such an aperture can be a lateral port defined by a side wall of the probe 100 providing an outlet for the delivery of cooling fluid, anesthetic, or any other treatment compound to a target treatment site in a body. Alternatively, the at least one aperture maybe located at the distal end 106 of the probe 100.

In some embodiments, a proximal end of the probe 100 can include a strain relief, which can additionally include a grip running from the proximal end to the distal end of the strain relief. A strain relief can be, for example, a soft flexible bend relief able to support any cable or tubing exiting the proximal end of the probe 100.

As mentioned hereinabove, the size and/or geometry of electrically insulating region 116 and the conductive portion 118 may differ depending on the specific application. As disclosed in U.S. Patent Application Publication No. 2007/0156136 to Godara, et al. and U.S. Pat. No. 7,819,869 to Godara, et al., which are incorporated herein by reference, when sufficient energy is delivered from an energy source through an active electrode to a tissue of a patient's body, a lesion may form in the tissue wherein the size, shape, and location of the lesion are at least partially dependent on the size and/or geometry of the active electrode.

Exemplary embodiments of probes 100 having a conductive portion 118 of various geometries, and being of between about 16 AWG and about 19 AWG, and examples of lesions 502 that may be formed therefrom are illustrated in FIGS. 5A to 5D, by way of non-limiting example only. Referring first to FIG. 5A, when conductive portion 118 of probe 100 is elongate, for example having a length of between about 4 mm and about 6 mm a substantially oblate lesion 502 may form around conductive portion 118. Due to edge effects, the distribution of energy may not be equal around all portions of the conductive portion 118, and a large portion of the current may exit the conductive portion 118 in the region closest to the electrically insulated portion 116. Thus, the widest portion of the lesion may form in the area adjacent the electrically insulated portion 116. In use, such a conductive portion may be positioned such that it lies substantially parallel to the surface of the tissue to be lesioned (target site) in order to provide maximum efficacy.

Referring now to FIG. 5B, when the electrically conductive portion 118 of the probe 100 is shortened and, for example, has a length of between about 2 mm and about 4 mm, a substantially more rounded lesion 502 may form around the conductive portion 118. Due to the shorter length of the conductive portion 118, the lesion 502 may extend distally further from the probe 100 than the lesion shown in FIG. 5A.

In some embodiments, the electrically insulated portion may extend substantially from the proximal region 108 of the probe 100 to the distal end of probe 100. For example, the electrically insulated portion 116 may terminate at the distal face of the probe such that the distal face 107 of the probe 100 includes at least one electrically exposed conductive portion 118. As will be apparent to the person skilled in the art, depending upon the geometry of the probe, the electrically insulated portion may terminate slightly proximal to the distal face so long as the energy delivery remains substantially distal. In some embodiments, a portion of the distal face 107 can include at least one conductive portion 118 as shown, for example, in FIGS. 2B-2D. Referring now to FIG. 5C, a probe 100 having a distal face 107 that includes electrically exposed conductive portion 118 is shown. In such embodiments, if distal face 107 is rounded (as shown in FIG. 5C), the rounded face or surface can include the conductive portion 118; if the distal face 107 is flat, the flat surface can include the conductive portion 118, and so on. In these embodiments, a lesion 502 may form wherein the lesion forms substantially distal to the distal face 107, for example, such that the majority of the lesion 502 is located distal to the distal face 107 of the probe 100, and the shape of the lesion 502 may be substantially rounded, for example the ratio of the length of the lesion 502 (i.e., the dimension along the longitudinal axis of the probe 100) to the width of the lesion 502 (i.e., the dimension perpendicular to the longitudinal axis of the probe 100) may be about 1:1. In use, such a probe 100 may be positioned such that it is oriented substantially perpendicular or generally upstanding to the target site or surface of the tissue to be lesioned (i.e., such that the tissue to be lesioned is generally distal to the probe 100, whereby the lesion 502 may extend distally from the probe 100 to the target tissue. This can provide significant advantages in a region of the body such as the sacroiliac region having a rough or uneven surface, because the conductive portion 118 can be positioned to lesion tissue (e.g., target nerve tissue such as a nerve 120) disposed in rifts and valleys between bony structures, or in fissures or grooves in the surface of a bony structure, as is described in detail below. In further embodiments, the conductive portion 118 may be offset from an axis of the probe 100 such that the electrically exposed conductive portion 118 is not symmetrical about the axis of the probe 100, as shown for example in FIG. 5D.

With reference now to FIG. 6, systems can include one or more of: one or more devices (e.g., percutaneous probes) 100 as already discussed in detail above; one or more introducer apparatuses 604; one or more dispersive return electrodes (not shown); one or more sources of cooling, for example pumps 610; one or more energy sources, for example, an energy generator 608; a controller 700; and one or more connecting means, for example tubes 312 and/or cables 612.

The introducer apparatus may aid in inserting the probe 100 into a patient's body. The introducer apparatus can include a hollow elongate introducer/cannula 604 and an obturator 606. In this embodiment, as mentioned above, the introducer 604 may be useful for facilitating insertion of the device into the patient's body. For example, the introducer 604 and/or the obturator 606 may be substantially stiff or rigid, such that the introducer apparatus may assist in piercing skin or other body tissues. The obturator 606 may be structured to cooperatively engage the introducer 604. In other words, the obturator 606 may be sized to fit within the lumen of the introducer 604 and can include means for securing the obturator 606 to the introducer 604. In one embodiment, when the obturator 606 is fully disposed within the introducer 604, the obturator 606 sufficiently occludes the lumen of the introducer 604 such that tissue is prevented from entering the lumen when the introducer apparatus is inserted into the body. In some embodiments the distal end of the obturator 606 may be sharp or pointed. In these embodiments, the distal end of the obturator 606 may be conical, beveled, or, more specifically, tri-beveled. The lengths of the obturator 606 and the introducer 604 may vary depending on the application. In one embodiment, the introducer 604 may be sized such that its distal end can reach the target tissue within the body while the proximal end remains outside of the body. In some embodiments, the introducer 604 can be between about 5.5 inches (13.97 cm) and about 7.5 inches (19.05 cm) in length, and obturator 606 may be between about 5.5 inches (13.97 cm) and about 7.5 inches (19.05 cm) in length. More specifically, the introducer 604 may be about 6.4 inches (16.26 cm) in length, and the obturator 606 may be about 6.6 inches (16.76 cm) in length. The obturator 606 may be slightly longer than the introducer 604, so that the distal end of the obturator 606 may protrude from the introducer 604 when fully disposed. In some embodiments, obturator 606 may be substantially longer than the introducer 604, and may be visible under fluoroscopy, such that it may aid in visualizing the location of lesion formation when a cooled probe is used. Further details regarding this embodiment are disclosed in U.S. Patent Application Publication No. 2009/0024124 to Lefler, et al., which is incorporated herein by reference. The lumen of the introducer 604 can also be sized to accommodate the diameter of the probe 100, while remaining as small as possible in order to limit the invasiveness of the procedure. In a specific embodiment, the proximal regions of the introducer 604 and the obturator 606 are structured to be locked together with a hub or lock.

In one embodiment, introducer 604 and the obturator 606 can be made from stainless steel. In other embodiments, the introducer 604, the obturator 606, or both may be made from other materials, such as nickel-titanium alloys for example.

Furthermore, in some embodiments, the obturator 606 can include a means for connecting the obturator 606 to an energy generator 608, for example a wire or cable. In such embodiments, the obturator 606 may be operable to measure the impedance of tissue as the introducer apparatus is inserted into the patient's body. In addition or alternatively, the obturator 606 may be operable to deliver stimulation energy to a target tissue site, as described further herein below.

In some embodiments, the probe 100 may be structured to be operatively connected to an energy source, for example the energy generator 608, where the controller 700 can measure the energy delivered to the probe by the energy generator 608. Meanwhile, the controller 700 can also be utilized to adjust the power supplied to the probe 100 by the energy generator 608 based on energy measurements obtained by the controller 700.

The connecting means 612 for connecting the probe 100 to the energy generator 608 can include any component, device, or apparatus operable to make one or more electrical connections, for example an insulated wire or cable. In one embodiment, the connecting means 612 can include an electrical cable terminating at the hub 114 as well as a connector at a proximal end thereof. The connector may be operable to couple to the energy generator 608 directly or indirectly, for example via an intermediate cable. At least one wire or other electrical conductor associated with the cable 612 may be coupled to a conductive portion of the shaft 122, for example by a crimp or solder connection, in order to supply energy from the energy generator 608 to the shaft 122. In one specific embodiment, a 4-pin medical connector may be used to connect the cable 612 to an intermediate cable (not shown), which may be further attached to a 14-pin connector capable of being automatically identified when connected to the energy generator 608.

The energy generator 608 may produce various types of energy, for example microwave, ultrasonic, optical, or radio-frequency electrical energy. In some embodiments, the energy generator 608 may produce radiofrequency electrical current, having a frequency of between about 1 kHz and about 1000 kHz, at a power of between about 1 Watts and about 50 Watts.

In some embodiments, the generator 608 can include a display means incorporated therein. The display means may be operable to display various aspects of a treatment procedure, including but not limited to any parameters that are relevant to a treatment procedure, such as temperature, power or impedance, and errors or warnings related to a treatment procedure. Alternatively, the energy generator 608 can include means for transmitting a signal to an external display. In one embodiment, the energy generator 608 may be operable to communicate with one or more devices, for example with one or more probes 100 and/or one or more sources of cooling, for example pumps 610. Such communication may be unidirectional or bidirectional depending on the devices used and the procedure performed. An example of an RF generator that may be used as part of a system of the present invention is the Pain Management Generator (PMG) of Baylis Medical Company Inc. (Montreal, QC, Canada). Further details regarding embodiments of energy sources are disclosed in U.S. Pat. No. 8,882,755 to Leung, et al. and U.S. Pat. No. 7,258,688 to Shah, et al., both of which are previously incorporated herein by reference.

As an example of communication between the energy generator 608 and other devices in a system, the energy generator 608 may receive temperature measurements from one or more temperature sensing devices 112. Based on the temperature measurements, the energy generator 608 may perform some action, such as modulating the power that is sent to the probe(s). For example, power to the probe(s) could be increased when a temperature measurement is low or decreased when a measurement is high, relative to a predefined threshold level. If more than one probe is used, the generator may be operable to independently control the power sent to each probe depending on the individual temperature measurements received from the temperature sensing devices associated with each probe. In some cases, the energy generator 608 may terminate power to one or more probe(s) 100. Thus, in some embodiments, the energy generator 608 may receive a signal (e.g., temperature measurement) from one or more probe(s), determine the appropriate action, and send a signal (e.g., decreased or increased power) back to one or more probe(s).

Alternatively, if one or more cooling means (i.e., sources of cooling), includes one or more pumps 610, for example peristaltic pumps, the one or more pumps 610 may communicate a cooling fluid flow rate to the energy generator 608 and may receive communications from the energy generator 608 instructing pump(s) 610 to modulate this flow rate depending, for example, on temperature measurements received by the energy generator 608. In some embodiments, the pump(s) 610 may respond to the energy generator 608 by changing the flow rate or by turning off for a period of time. The pumps may be turned off in order to allow the temperature of the tissue surrounding the probe 100 to reach equilibrium, thereby allowing a more precise determination of the surrounding tissue temperature to be made. In addition, when using more than one probe 100, in embodiments where the energy generator 608 does not control each of the probes 100 independently, the average temperature or a maximum temperature in the temperature sensing devices 112 associated with probe(s) 100 may be used to control the cooling means.

As mentioned above, in some embodiments, one or more peristaltic pumps 610 may be used to supply a cooling fluid to and return a cooling fluid from probe(s) 100. In other embodiments, other types of pumps may be used. Examples include, but are not limited to, a centrifugal pump or a piston pump. As mentioned above with respect to temperature control, controlling the delivery of a cooling fluid, or other cooling means, may be performed for each probe independently or the cooling may be controlled based on an average temperature measurement or a measurement recorded from one probe, for example. Further details regarding the cooling source are provided in U.S. Pat. No. 8,882,755 to Leung, et al. and U.S. Pat. No. 7,163,536 to Godara, et al.

In addition, the controller 700 can determine the location of one or more zones of effective tissue alteration of the target tissue as a result of energy delivered by the probe 100 via various parameters. For instance, the controller 700 can determine and/or identify boundaries for: (1) a primary zone 502 that corresponds to the lesion as visible by the unaided eye, where substantial coagulation of collagen has occurred, (2) a secondary zone 504 that corresponds to an area of effective tissue alteration as evidenced by coagulation of collagen, albeit to a lesser extent than in the primary zone 502, where the second zone 504 can be referred to as an intermediate/transition zone or a zone that is not visible to the unaided eye, and (3) a tertiary zone 506 that may also exhibit some extent of coagulation of collagen and/or other cellular changes/inflammatory responses/etc. but to a lesser extent than the primary zone and secondary zone, indicating that the tertiary zone also corresponds to an area of effective tissue alteration, where tissue alteration in the primary zone and or secondary zone may not be needed to achieve the desired treatment result. Moreover, the controller 700 can also identify a fourth zone 508 that corresponds to tissue unaffected by the denervation procedure, as evidenced by minimal to no collagen coagulation or other biochemical changes/physiological responses. In addition, the primary zone 502 can be adjacent or proximal to the component for percutaneously applying energy (e.g., at the visible lesion) and the secondary zone 504 can be adjacent or substantially envelope the primary zone 502. Further, the tertiary zone 506 can be adjacent or substantially envelope the secondary zone 504, and the fourth zone 508 of unaffected tissue can be adjacent or substantially envelope the tertiary zone 506.

However, it is also to be understood that each of these zones may encompass, include, or overlap with any of the other zones. For instance, the secondary zone 504 may include or overlap the primary zone, while the tertiary zone 506 may include or overlap the secondary zone 504 and/or the primary zone 502. Likewise, the level of tissue alteration associated with the secondary zone 504 may extend into the primary zone 502, and the level of tissue alteration associated with the tertiary zone 506 may extend in to the secondary zone 504 and the primary zone 502. For example, the primary zone 502 can include the levels of tissue alteration associated with the secondary zone 504 and/or the tertiary zone 506 in addition to having a visible lesion.

The operation of the system may be automatically controlled via the controller 700 based on certain parameters, for example, based on a measurement of a property of a component of is the system itself or of a property of the tissue being treated (e.g., the amount of energy delivered by the energy generator 608 to the probe 100, the boundaries for the various zones 502, 504, 506, and 508 of denervation, etc.). Moreover, the amount and type of energy (standard vs. cooled) delivered during a treatment procedure can be correlated with the level and/or extent of tissue alteration desired as determined via the amount of collagen coagulation, the level of immune cell infiltration, the amount of protein changes, or other suitable biomarker analysis (e.g., perineurial collagen coagulation, epineurial collagen coagulation, endoneurial collagen coagulation, coagulative necrosis, vascular necrosis, axonal degeneration, inflammation, subacute histiocytosis, hypertrophy, hyperplasia, immune cell activation, schwann cell infiltration, nerve fibrosis, macrophage infiltration, growth cone sprouting, structural integrity, sensory threshold, biochemical signaling, cell body response, dorsal root ganglia response, etc.) from multiple samples of data in order to determine the relationship between the amount and type of energy delivered and the extent of tissue alteration in order to control the extent of tissue alteration in a patient being treated. For example, in one particular embodiment, the controller 700 can be programmed to deliver up to about 100 kilojoules of cooled radiofrequency energy over a suitable time period, such as a time period of up to about 150 seconds or longer, in order to denervate or ablate a region that is within about 20 millimeters of the probe, where the region includes one or more zones of effective tissue alteration (e.g., denervation or ablation). In another particular embodiment, the controller 700 can be programmed to delivery up to about 100 kilojoules of standard radiofrequency energy over a suitable time period, such as a time period of up to about 90 seconds or longer in order to denervate a region that is within about 10 millimeters of the probe.

Moreover, in other embodiments, the controller 700 can be programmed to deliver from about 25 joules to about 100 kilojoules, such as from about 50 joules to about 75 kilojoules, such as from about 75 Joules to about 50 kilojoules, such as from about 80 joules to about 25 kilojoules of standard radiofrequency energy over a time period ranging from about 30 seconds to about 120 seconds, such as from about 45 seconds to about 110 seconds, such as from about 60 seconds to about 100 seconds to a target nerve of a human. In another embodiment, the controller can be programmed to deliver about 1 joules/second (J/s) to about 6 J/s, such as from about 1.5 J/s to about 5 J/s, such as from about 2 J/s to about 4 J/s of standard radiofrequency ablation energy to a target nerve of a human.

Further, in still other embodiments, the controller 700 can be programmed to deliver from about 25 joules to about 100 kilojoules, such as from about 100 joules to about 80 kilojoules, such as from about 350 joules to about 60 kilojoules, such as from about 375 joules to about 40 kilojoules of cooled radiofrequency energy over a time period ranging from about 45 seconds to about 180 seconds, such as from about 60 seconds to about 170 seconds, such as from about 75 seconds to about 160 seconds to a target nerve of a human. In another embodiment, the controller can be programmed to deliver about 2 joules/second (J/s) to about 8 J/s, such as from about 2.5 J/s to about 7 J/s, such as from about 3 J/s to about 6 J/s of cooled radiofrequency ablation energy to a target nerve of a human.

Figure 8:
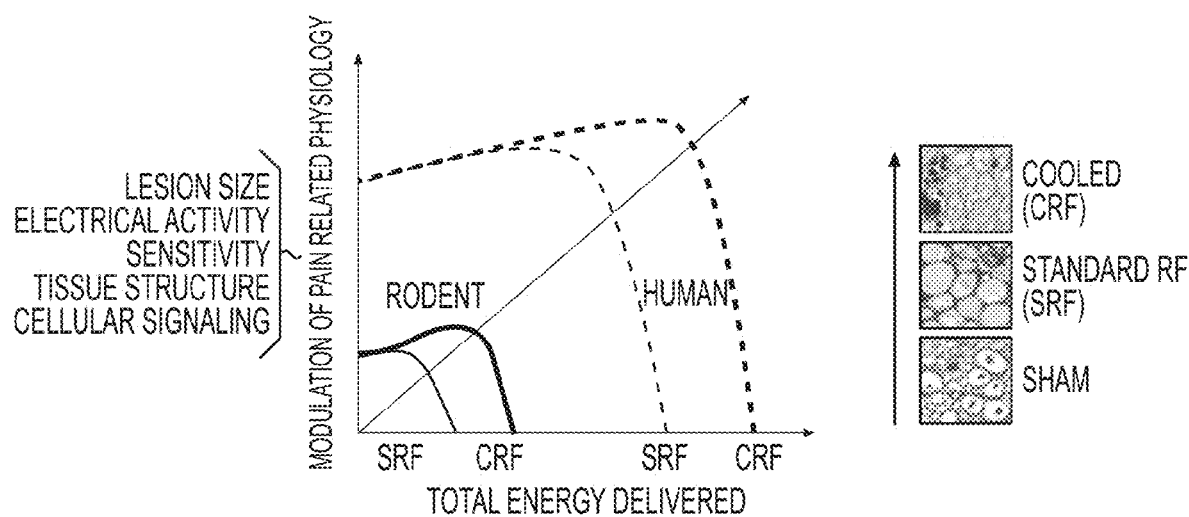
FIG. 8 shows the effects of increased energy. The graph at the left illustrates the magnitude and extent of physiological changes (e.g., lesion size, electrical activity, sensitivity, tissue structure, and cellular signaling) based on the total energy delivered using a standard radiofrequency (SRF) probe and a cooled radiofrequency (CRF) probe. The histological images at the right illustrate that cellular damage increases with increased energy.

Generally, the total amount of energy delivered during the ablation procedure can correlate proportionally to the size of the lesion as shown in FIG. 8 as discussed in more detail below. In addition to the total energy delivered, the rate at which the energy is delivered or deposited into the tissue as measured in Joules/second can also impact the overall lesion size.

Turning now to FIGS. 7-12, different characteristics of a system utilizing a standard probe 101 and a system utilizing a cooled probe 103 are described in more detail.

Figure 7:
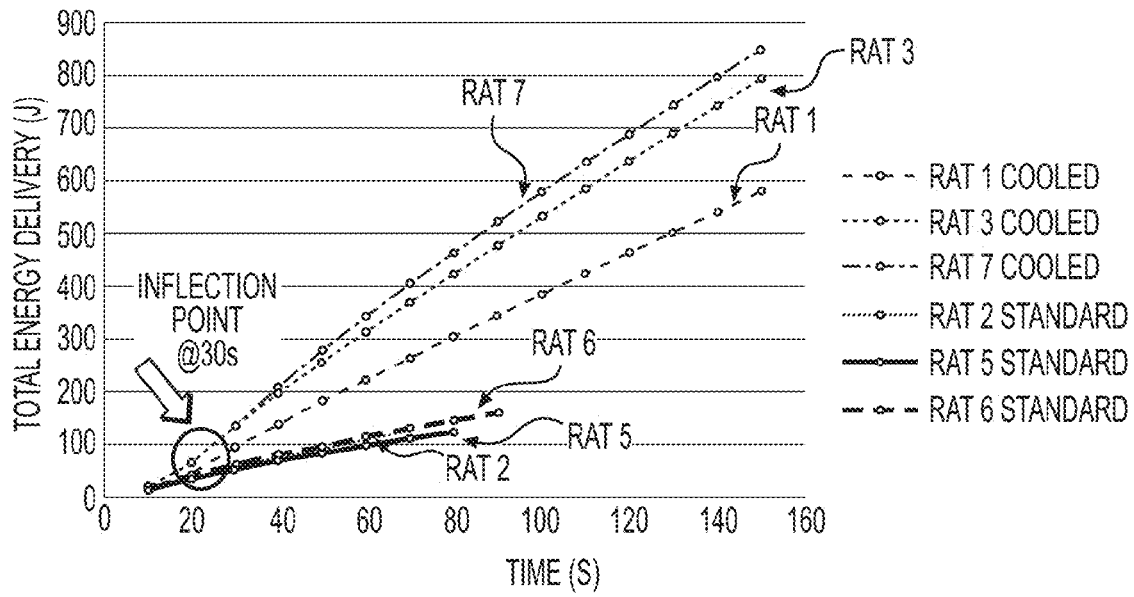
FIG. 7 is a graph comparing the total energy delivered in Joules (J) during standard radiofrequency ablation procedures and cooled radiofrequency ablation procedures.

FIG. 7 is a graph comparing the total energy delivered in Joules (J) during standard radiofrequency ablation procedures and cooled radiofrequency ablation procedures. As shown, the standard radiofrequency ablation procedures resulted in the delivery of smaller amounts of energy in Joules (J) over a period ranging from about 10 seconds to about 160 seconds compared to cooled radiofrequency ablation. Specifically, when utilizing a standard probe, the amount of energy delivered to the target nerve tissue during the radiofrequency frequency ablation procedure can range from about 25 joules to about 100 kilojoules, such as from about 50 Joules to about 75 kilojoules, such as from about 75 Joules to about 50 kilojoules, such as from about 80 Joules to about 25 kilojoules. On the other hand, when using a cooled radiofrequency ablation probe, the amount of energy delivered to the target nerve tissue during the radiofrequency ablation procedure can range from about 25 joules to about 100 kilojoules, such as from about 100 joules to about 80 kilojoules, such as from about 350 joules to about 60 kilojoules, such as from about 375 Joules to about 40 kilojoules. Further, cooled radiofrequency ablation can result in the delivery of about 1.25 times to about 3.5 times, such as from about 1.5 times to about 3 times, such as from about 2 times to about 2.5 times the energy to the target nerve tissue compared to standard radiofrequency ablation.

FIG. 8 is a graph illustrating the magnitude and extent of physiological changes (e.g., lesion size, electrical activity, sensitivity, tissue structure, and cellular signaling) during an ablation procedure of a nerve based on the total energy delivered using a standard radiofrequency (SRF) probe and a cooled radiofrequency (CRF) probe for both rodents and humans. As shown, as the total energy delivered is increased for both SRF probes and CRF probes, the lesion size is increased, and the lesion size for CRF probes is larger than the lesion size for SRF probes. Generally, the total energy delivered is higher for CRF probes compared to SRF probes for both clinical settings in humans and optimized parameters for rodents. Further, as the total energy delivered increases, the amount of cellular damage increases based on a comparison of stained tissue sample that was ablated with the CRF and SRF probes compared to a control sham tissue sample.

Figure 9:
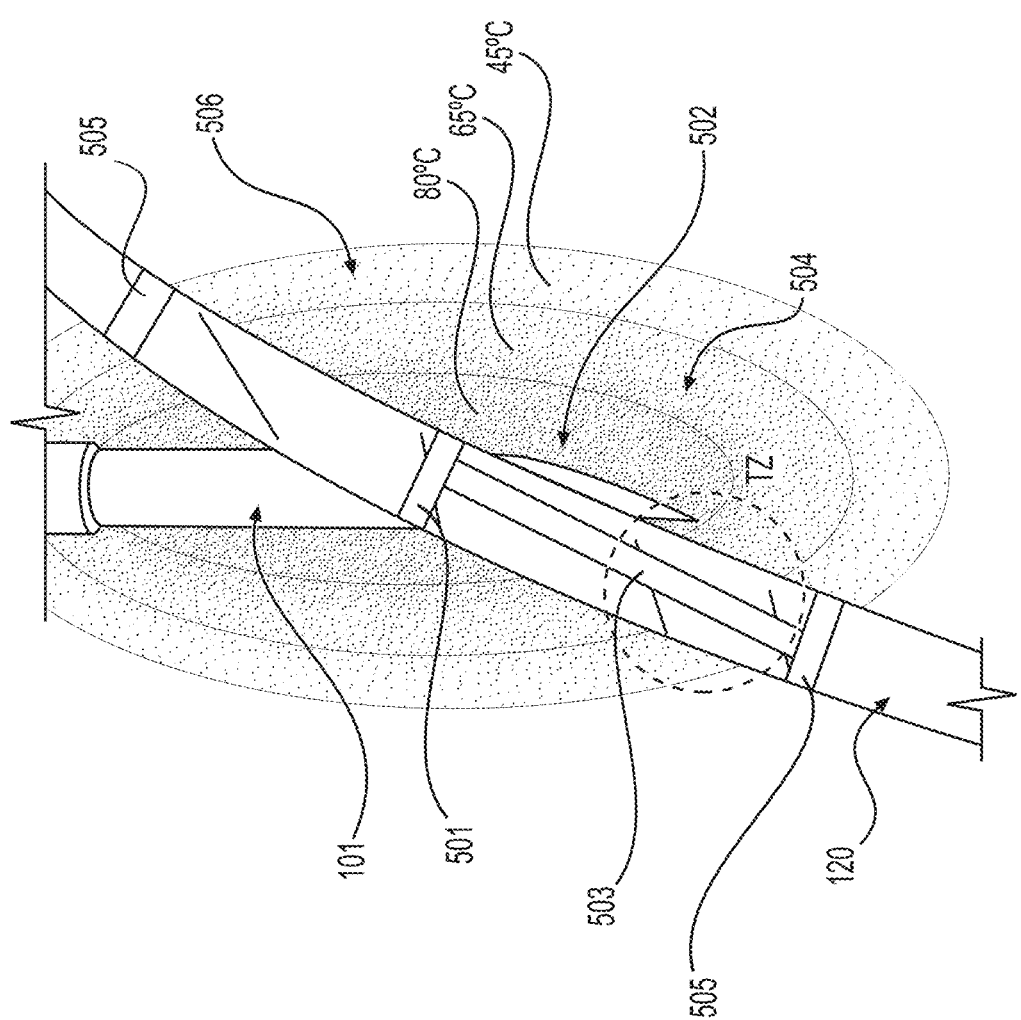
FIG. 9 is a schematic illustrating different zones of a lesion formed around a nerve during a standard radiofrequency ablation procedure due to the thermal energy profile. TZ indicates the transition zone.

FIG. 9 is a schematic illustrating a lesion 502 formed during a standard radiofrequency ablation procedure of a nerve with a standard probe 101, which can be based on the energy levels delivered in FIG. 7 or FIG. 8. As shown, the ablation or denervation area is generally oval or elliptical in shape around the standard probe 101. The treated nerve 120 has been effectively denervated at the visible lesion 502 (e.g., the primary zone), a secondary zone 504 that substantially envelopes the primary zone 502, and a tertiary zone 506 that substantially envelopes the secondary zone 504. Further, it can be verified that the three zones 502, 504, and 506 include effectively denervated nerve tissue in the nerve 120 based on the presence of coagulated collagen in each of the zones, or based on the volumetric size of the lesion as detected by in vivo imaging methods such as MRI. Areas of tissue located in the primary zone (for example, marked by band 501) could be expected to be altered to a first level. Areas of tissue located in the secondary (or transition) zone (for example, marked by band 503) could be expected to be altered to a second level. The second level of alteration in the transition zone may decrease along the length of the band 503 (moving away from band 501). Areas of tissue located in the tertiary zone (for example, marked by band 505) could be expected to be altered to a third level. Placement of bands 501, 503, and 505 is approximate and not meant to be limiting. Meanwhile, the absence of coagulated collagen would indicate the nerve tissue was not denervated or that the area of tissue being treated was not ablated or otherwise altered.

Figure 10:
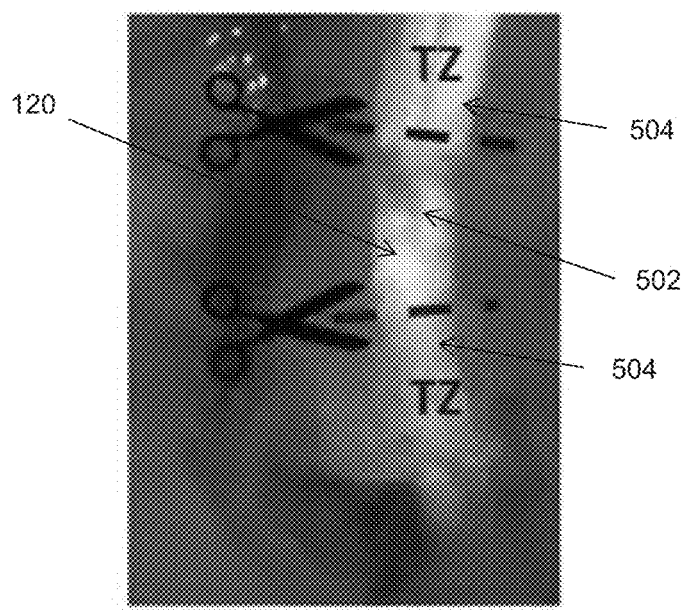
FIG. 10 is a photograph illustrating the appearance of nerve tissue after undergoing the standard radiofrequency ablation procedure of FIG. 9.

FIG. 10 is a photograph illustrating the appearance of a nerve 120 after undergoing the standard radiofrequency ablation procedure of FIG. 9, where the nerve 120 is effectively denervated at the visible lesion (e.g., primary zone) 502 and at the secondary zone 504 (e.g., intermediate/transition zone TZ) enveloping or surrounding the lesion 502.

Figure 11:
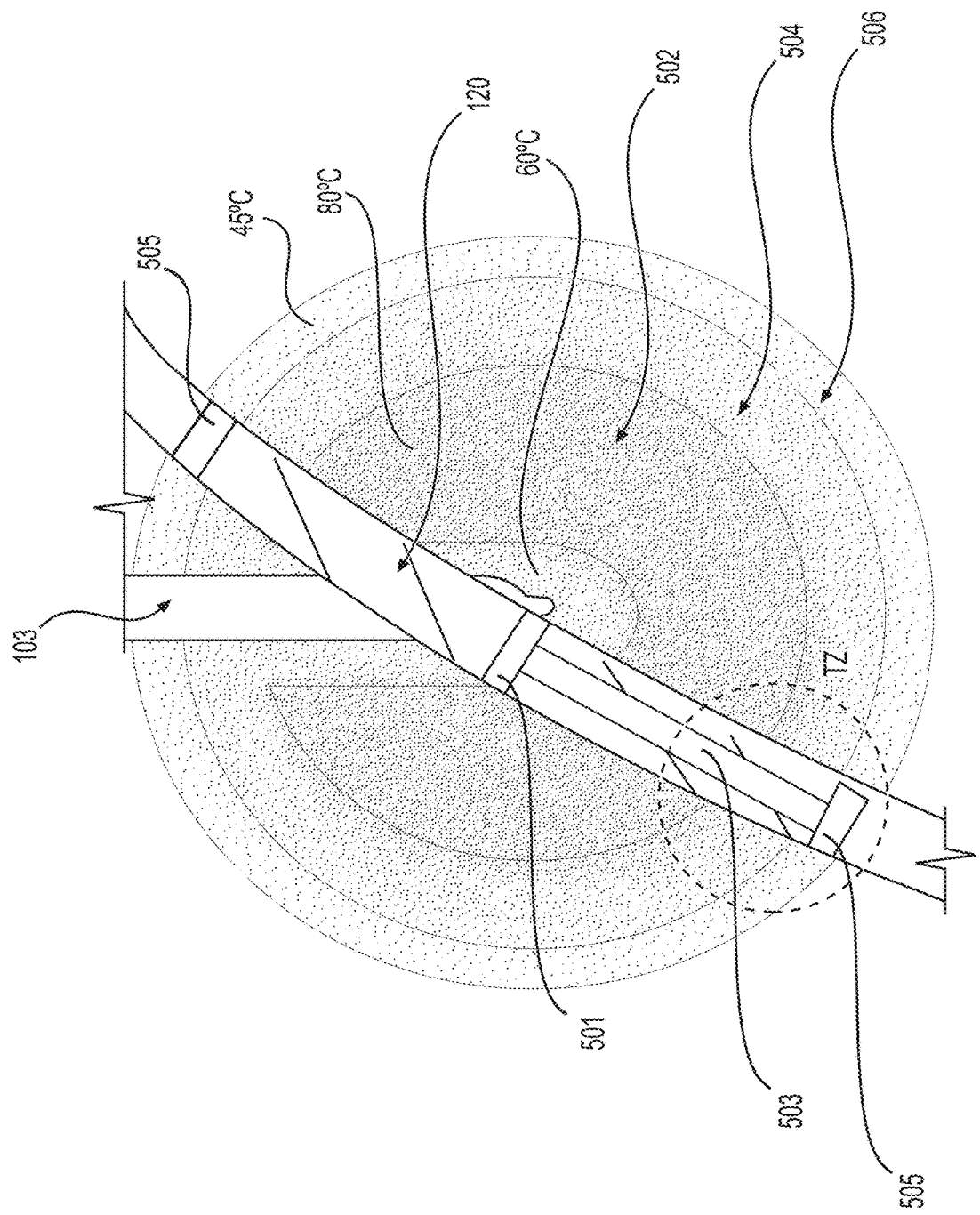
FIG. 11 is a schematic illustrating different zones of a lesion formed around a nerve during a cooled radiofrequency ablation procedure. TZ indicates the transition zone.

FIG. 11 is a schematic illustrating a lesion 502 formed during a cooled radiofrequency ablation procedure with a cooled probe 103, which can be based on the energy levels delivered in FIG. 7 or FIG. 8. As shown, the ablation or denervation area is generally round in shape around the cooled probe 103 due to the cooled probe's unique properties and physics. The ablation or denervation area is larger in area than the denervation area associated with the standard probe 101. The treated nerve 120 has been effectively denervated at the visible lesion 502 (e.g., the primary zone), a secondary or intermediate/transition zone 504 that substantially envelopes the primary zone 502, and a tertiary zone 506 that substantially envelopes the secondary zone 504. Further, it can be verified that the three zones 502, 504, and 506 include effectively denervated nerve tissue in the nerve 120 based on the presence of coagulated collagen in each of the zones. Areas of tissue located in the primary zone (for example, marked by band 501) could be expected to be altered to a first level. Areas of tissue located in the secondary (or transition) zone (for example, marked by band 503) could be expected to be altered to a second level. The second level of alteration in the transition zone may decrease along the length of the band 503 (moving away from band 501). Areas of tissue located in the tertiary zone (for example, marked by band 505) could be expected to be altered to a third level. Placement of bands 501, 503, and 505 is approximate and not meant to be limiting. Meanwhile, the absence of coagulated collagen would indicate the nerve tissue was not denervated.

Figure 12:
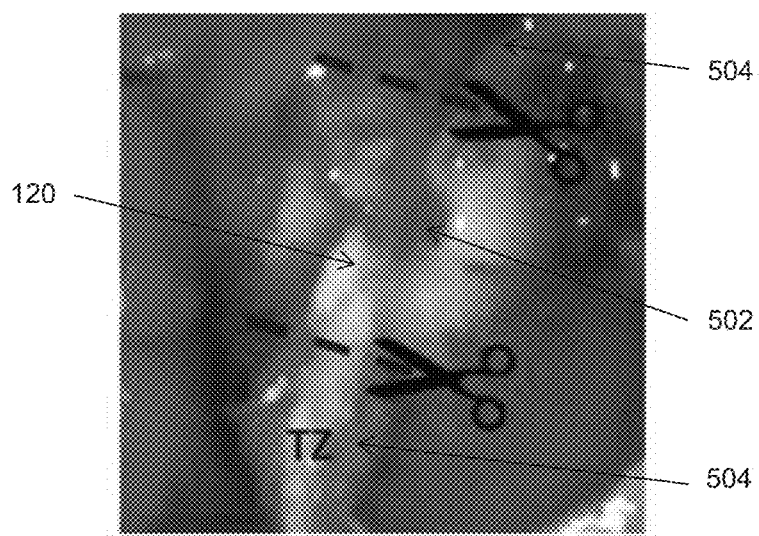
FIG. 12 is a photograph illustrating the appearance of nerve tissue after undergoing the cooled radiofrequency ablation procedure of FIG. 11.

FIG. 12 is a photograph illustrating the appearance of a nerve 120 after undergoing the cooled radiofrequency ablation procedure of FIG. 11, where the nerve 120 is effectively denervated at the visible lesion (e.g., primary zone) 502 and at the secondary zone 504 (e.g., intermediate/transition zone TZ) enveloping or surrounding the lesion 502.

Figure 13:
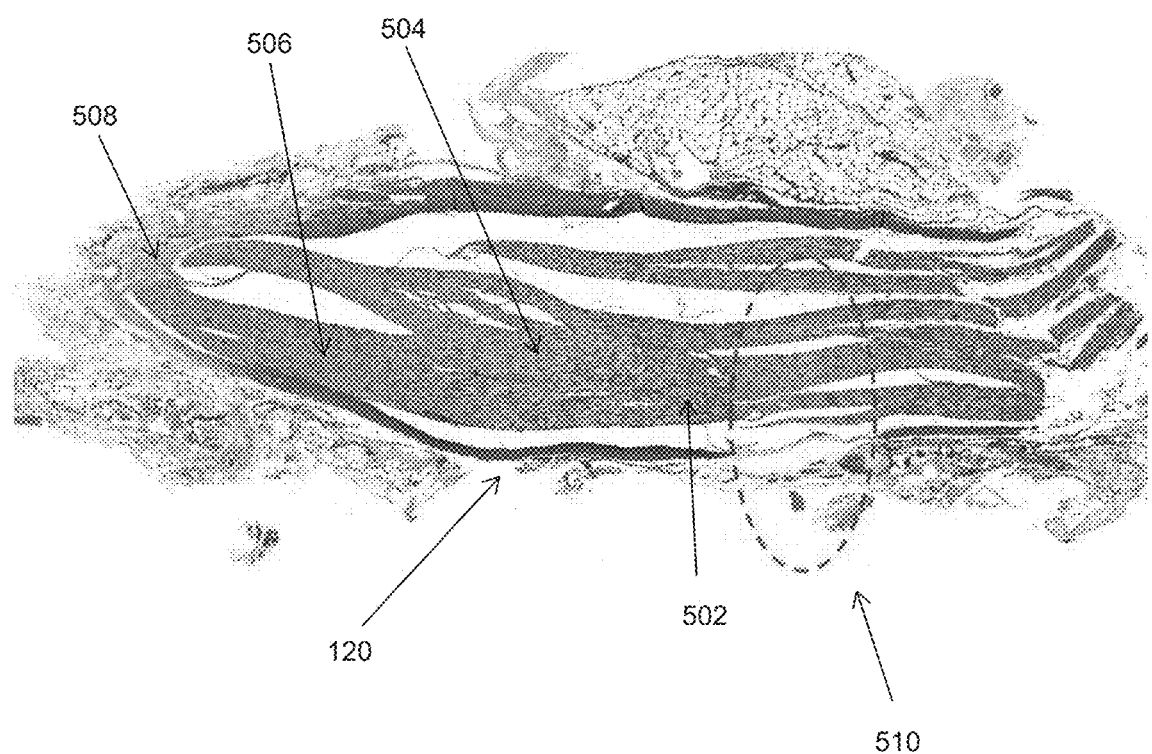
FIG. 13 is a representative image of a histologically stained sample of a nerve after undergoing the cooled radiofrequency ablation procedure of FIG. 11, where the sample was stained for the presence of collagen.

FIG. 13 is a representative, low magnification histologic image of a Hematoxylin & Eosin (H&E) stained sample of a nerve 120 after undergoing the cooled radiofrequency ablation procedure of FIG. 11, where the sample was stained for the presence of collagen (dark purple stain). As shown, the effective area of denervation includes a visible lesion (e.g., primary zone) 502 that includes coagulated collagen, a secondary zone 504 that also includes coagulated collagen but to a lesser extent than the primary zone 502, a tertiary zone 506 that can also include coagulated collagen but to a lesser extent than the secondary zone 504 and/or other biochemical changes and/or physiological responses, and a fourth zone 508 that includes tissue in the nerve 120 that has been unaffected by the cooled radiofrequency ablation procedure. Further, a subzone 510 is also present that represents a cooled region that has a lesser extent of collagen coagulation than surrounding areas outside the dashed oval. The subzone 510 represents the region immediately adjacent the cooled probe/nerve interface as shown in FIG. 11, where this subzone 510 is not present in tissue samples where the tissue underwent a standard radiofrequency ablation procedure. Moreover, the pink regions in FIG. 13 exhibit normal tissue where little to no coagulation is present and correspond with areas where the nerve tissue is unaffected and has not been lesioned, while the darker purple areas are indicative of more collagen coagulation and correspond with areas where the nerve tissue has been lesioned. Because the presence of these zones and the distance that the zones extend along a nerve can be correlated with the level and type of energy delivered, a medical professional can adjust the level and type of energy being delivered and know the extent of denervation achieved as a result.

Figure 14:
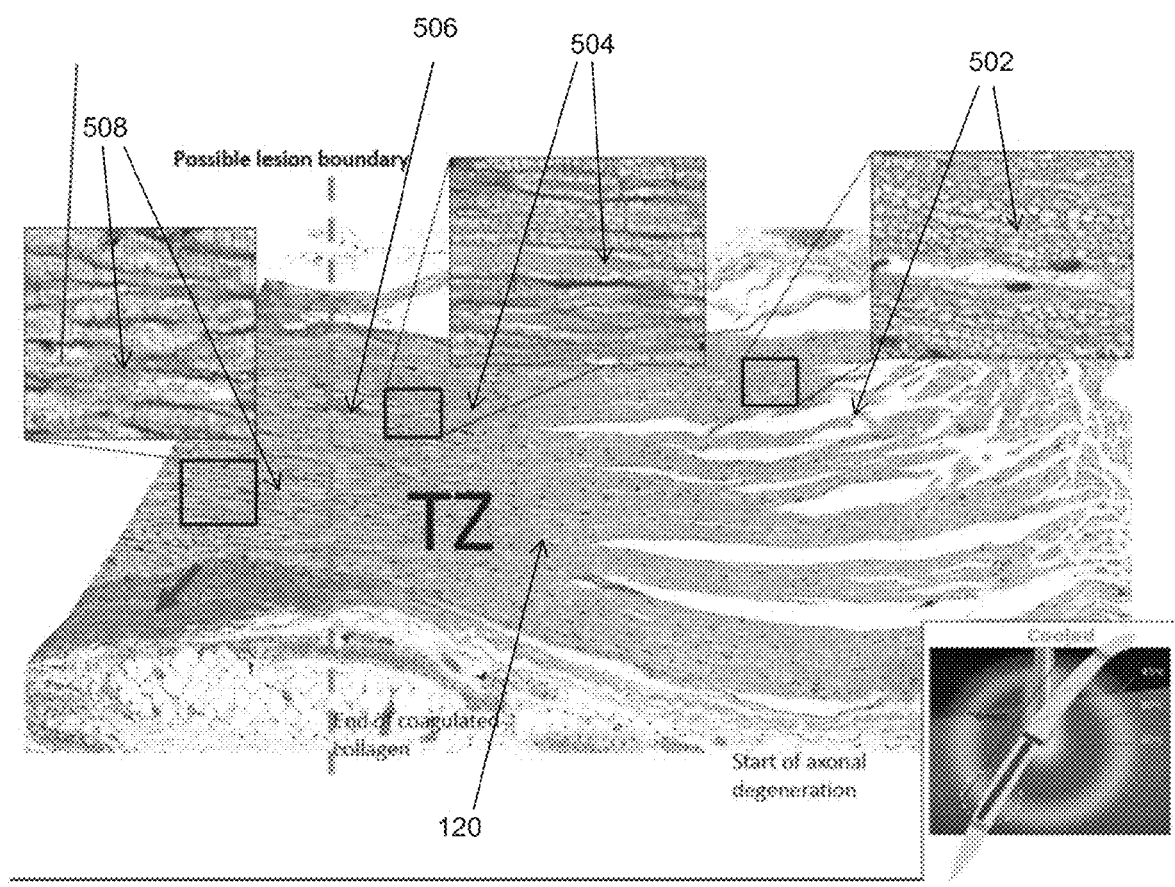
FIG. 14 is representative image of a histologically stained sample of a nerve after undergoing the cooled radiofrequency ablation procedure of FIG. 11, where the sample was stained for the presence of collagen.

FIG. 14 is another representative, higher magnification histologic image of a Hematoxylin & Eosin (H&E) stained sample of a nerve 120 after undergoing the cooled radiofrequency ablation procedure of FIG. 11, where the sample was stained for the presence of collagen. As shown, the effective area of denervation includes a visible lesion (e.g., primary zone) 502 that includes coagulated collagen, a secondary zone 504 that also includes coagulated collagen but to a lesser extent than the primary zone 502, a tertiary zone 506 that also includes coagulated collagen but to a lesser extent than the secondary zone 504, and a fourth zone 508 that includes tissue in the nerve 120 that has been unaffected by the cooled radiofrequency ablation procedure. Because the presence of these zones and the distance that the zones extend along a nerve can be correlated with the level and type of energy delivered, a medical professional can adjust the level and type of energy being delivered and know the extent of denervation achieved as a result.

The present invention may be better understood by reference to the following examples.

Example 1

In a rodent model, cooled radiofrequency (RF) energy and standard RF energy was applied using human clinical setting time frames (150 seconds for cooled RF and 90 seconds for standard RF) and at time frames normalized and optimized for the size difference between a human and a rodent (80 seconds for cooled RF and 50 seconds for standard RF). The amount of energy delivered to the target nerve in each condition is shown in Table 1, along with energy reduction and the rate of energy delivery in Joules/second for the normalized samples.

The first set is for Cooled RF and Standard RF procedures conducted under the normal "human" clinical conditions but in a small mammal (a laboratory rat). RF energy is applied for 150 seconds in the Cooled RF procedure and for 90 seconds in the Standard RF procedure. For Standard RF, the data generally show a "conventional" lesion of about 5 to 6 mm in diameter and an intermediate lesion of an additional 2 to 3 mm surrounding the "conventional" lesion on a proximal side (closest to the mammal's spine) and 10 to 17 mm on a distal side (closest to the mammal's foot). For Cooled RF, the data generally show a "conventional" lesion of about 8 to 9 mm in diameter and an intermediate lesion of an additional 4 to 9 mm surrounding the "conventional" lesion on a proximal side (closest to the mammal's spine) and 10 to 15 mm on a distal side (closest to the mammal's foot). This variability on the distal side (particularly for standard RF) is due to factors including anatomy, tissue characteristics, probe design, etc.

Referring to Table 1 below, the first and third columns of data were obtained from procedures in which the ablation conditions were "optimized" for appropriate ablation in a small mammal (a rat). Because the human "clinical" conditions are for a much larger mammal, such conditions tend to form much large lesions in the small mammal, leading to severe adverse events such severe damage (e.g., foot lesions). The ablation conditions were therefore "optimized" by shortening the time. RF energy is applied for only 80 seconds (vs. 150 seconds) in the Cooled RF procedure and for 50 seconds (vs. 90 seconds) in the Standard RF procedure. For Standard RF at the "optimized" conditions, the data generally show a "conventional" lesion of about 2 mm in diameter and an intermediate lesion of an additional 0.75 mm surrounding the "conventional" lesion on a proximal side (closest to the mammal's spine) and 0.85 mm on a distal side (closest to the mammal's foot). For Cooled RF at the "optimized" conditions, the data generally show a "conventional" lesion of about 2 mm in diameter and an intermediate lesion of an additional 0.9 mm surrounding the "conventional" lesion on a proximal side (closest to the mammal's spine) and 0.8 mm on a distal side (closest to the mammal's foot). This variability on the distal side is due to a number of factors including anatomy, tissue characteristics, etc. Meanwhile, data for the "optimized" conditions is more consistent. The energy delivery under "optimized" conditions for Standard RF is 110.5±21.9 Joules (JO over 50 second for a delivery rate of about 2.44 Joules/sec (J/s). The energy delivery under "optimized" conditions for Cooled RF is 267.8+97.2 J over 80 second for a delivery rate of about 4.87 J/s.

TABLE 1

Energy Delivery and Lesion Size for Cooled and Standard Radiofrequency Energy Delivery Using Clinical (Human) and Optimized Parameters

| Parameter | Type of Energy Delivered | | | |
|---|---|---|---|---|
| | Cooled RF 80 seconds | Cooled RF 150 Seconds | Standard RF 50 seconds | Standard RF 90 seconds |
| Total Energy Delivered in Rodent at Clinical Parameters (Joules) (Mean + SD) | — | 943.49 ± 311.8 | — | 257.72 ± 26.2 |
| Total Energy Delivered in Rodent at Optimized Parameters (Joules) (Mean + SD) | 497.8 ± 183.7 | — | 174.3 ± 38.4 | — |
| Energy Reduction from Clinical Parameters | 47.2% | — | 32.2% | — |
| Rate of Energy Delivery (Joules/sec) | 4.87 | 3.96 | 2.44 | 3.64 |
| Ablation Zone Length (mm) | 4.48 ± 3.6 (N = 3) | 5.9 ± 1.7 (N = 9) | 3.5 ± 1.99 (N = 6) | 3.9 ± 1.3 (N = 11) |
| Proximal Transition Zone Length (mm) | 1.59 (N = 2) | Not assessed | 1.93 (N = 2) | Not assessed |
| Distal Transition Zone Length (mm) | 1.89 (N = 2) | Not assessed | 1.68 (N = 2) | Not assessed |

In addition, tissue samples from the intermediate or transition zone were stained for the presence of CD11b, a marker indicating the presence of macrophage cells/immune cell infiltration. As shown in the chart below, the control sample that was not subjected to radiofrequency (RF) energy did not stain for the presence of CD11b in the area where a transition zone would have been located. Meanwhile, both of the tissue samples where standard RF energy and cooled RF energy were delivered did stain for the presence of macrophages in the intermediate or transition zone (e.g., the secondary zone of effective denervation that substantially envelopes the primary zone) surrounding the main lesion (e.g., the primary zone of effective denervation proximal to probe), although more macrophages were present in the secondary zone for the lesion formed via standard RF as compared to the secondary zone for the lesion formed by cooled RF. In any event, the presence of macrophages in the intermediate or transition zone indicates that effective denervation can occur in an area surrounding the visible lesion.

TABLE 2

Immune Cell Infiltration in the Transition Zone

| Energy Delivered | Presence of CD11b Marker Indicating Macrophage Presence |
| --- | --- |
| Control (No RF Energy Applied) | – |
| Standard RF Energy Applied | ++ |
| Cooled RF Energy Applied | + |

Example 2

Naïve male Lewis rats (300-350 g; 12 weeks old), which age approximately 1 human year every 2 weeks, were exposed to rodent-optimized sciatic nerve ablation parameters, SRF (50 s, 80° C.) or CRF (80 s, 60° C.) and evaluated for four weeks (2 human years). A follow-up study exposed male Lewis rats (300-350 g; 12 weeks old) to a pain phenotype in which local inflammation was induced via Freund's complete adjuvant (FCA) injection in the left hind paw prior to ablation (Larson et al.). All animals in both studies were evaluated for functional outcomes. Animals in the naïve (non-pain study) were evaluated via gastrocnemius, tibialis anterior, and foot muscle electromyography (EMG) for sciatic nerve axonal regeneration and muscle fiber reinnervation post-ablation (English et al.). Animals in the pain study were evaluated via von Frey for left hind paw mechanosensitivity before and after ablation (Chaplan et al.). At the conclusion of the study 35 days post-ablation, animals in the pain group were evaluated for calcitonin gene-related peptide (CGRP) expression in central and basolateral amygdala (Han et al.).

Figure 15:
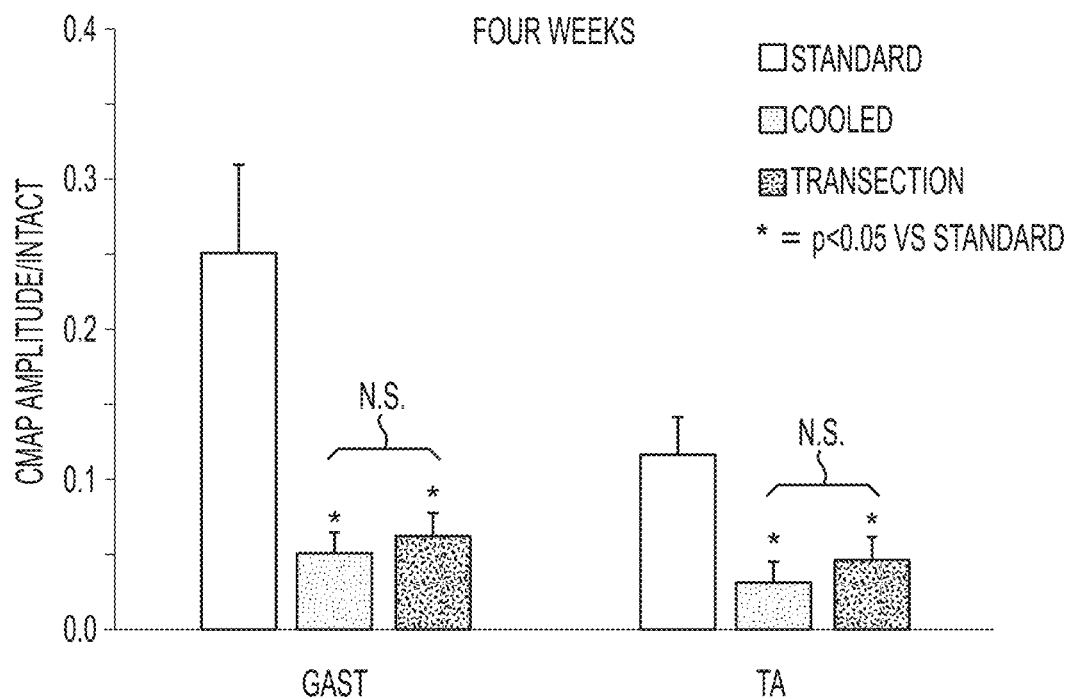
FIG. 15 is a graph depicting results from an EMG from the gastrocnemius (GAST) and tibialis anterior (TA) four weeks post-ablation in naïve animals. Data represented as percent of intact compound muscle action potential (CMAP, or M-response). Mean±standard error. *P<0.05 vs. standard RF. N=12 (SRF), 12 (CRF), 6 (Transection). Data are presented as a fraction of the "intact" response. Intact EMGs are taken prior to ablation. Each animal's M-response is normalized to its corresponding intact baseline M-response prior to ablation.
Figure 16:
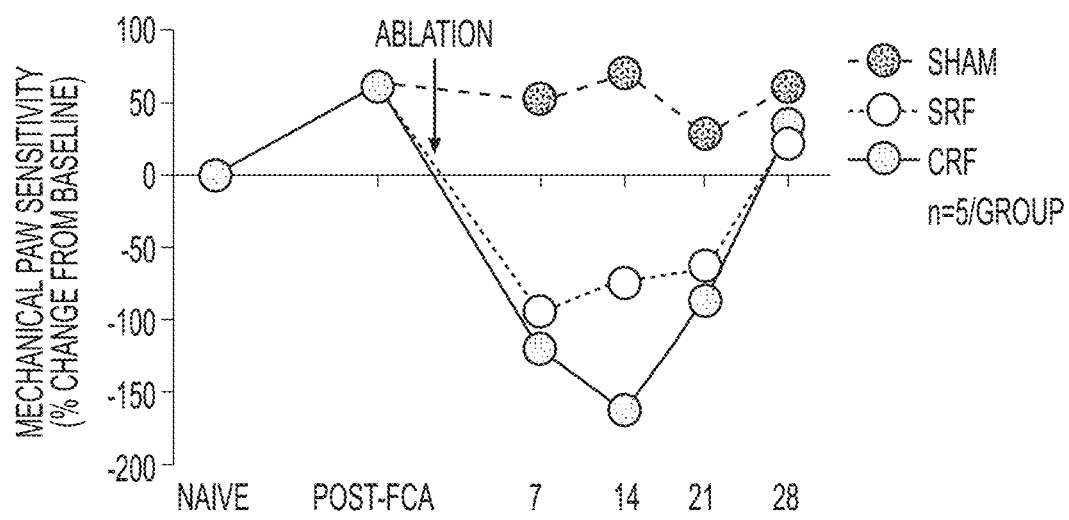
FIG. 16 is a graph depicting the results of a mechanical paw sensitivity assay over 28 days post-ablation in pain phenotype animals. Data represented as mean percent change from baseline where higher numbers represent greater sensitivity to the mechanical stimulus. N=5 per group.

Similar to animals in which the sciatic nerve is transected, naïve animals treated with CRF demonstrated reduced CMAP/M-response (EMG) in the gastrocnemius (GAST), tibialis anterior (TA), and foot muscles at T=0 compared to animals treated with SRF, and this difference persisted four weeks post-ablation (FIG. 15). Furthermore, in the pain study, animals treated with CRF demonstrated a greater reduction in mechanical sensitivity between T=0 and Day 21 compared to animals treated with SRF (FIG. 16).

Figure 30:
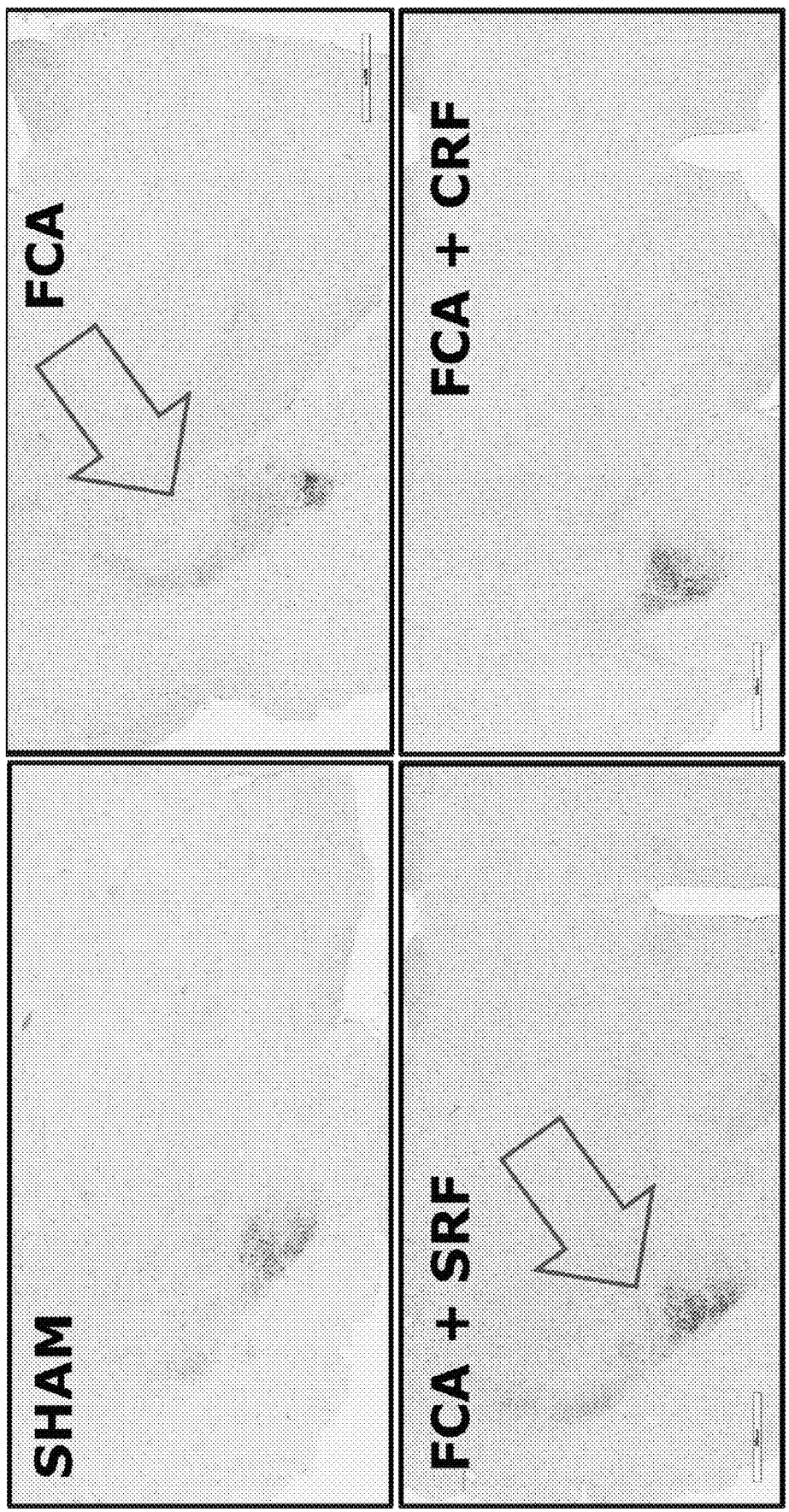
FIG. 30 shows immunohistochemistry images. Cross sections of the amygdala are stained (in brown) for CGRP, which causes inflammation in the brain and is a marker of pain. FCA=Freund's complete adjuvant. Scale bars=900 microns.

Immunohistochemistry in the central and basolateral amygdala six weeks post-ablation revealed attenuated CGRP expression in CRF-treated animals compared to both SRF-treated and untreated FCA-Sham controls, as demonstrated in FIG. 30. FIG. 30 shows immunohistochemically stained cross sections of the amygdala. Brown staining indicates CGRP, which causes inflammation in the brain and is a marker of pain. In the rat pain model, injecting the hind paw with FCA increases the expression of CGRP. Treatment with CRF reduces the CGRP present more significantly than treatment with SRF.

These studies demonstrate that CRF differentially impacts sciatic nerve return-to-function vs. SRF by delivering prolonged pain relief. CRF-treated naïve rats demonstrated significant reduction in M-response at T=0 and had persistently reduced EMG for 28 days compared to SRF-treated animals. Further, pain-phenotype animals had an extended period of reduced mechanical sensitivity following CRF treatment vs. SRF treatment up to 21 days post-ablation. Central nervous system neuroadaptations associated with chronic pain were attenuated after six weeks only in animals exposed to CRF, suggesting a differential neurophysiological response to CRF treatment vs. SRF treatment.

Collectively, these results suggest a prolonged beneficial effect of CRF vs. SRF. The results also suggest that the central biomarker expression associated with chronic pain is modulated by CRF, but not SRF, treatment. This indicates that chronic pain patients not only experience greater physical pain relief following CRF vs. SRF treatment, but CRF may also be effective in improving the negative emotional affect that is so frequently associated with chronic pain.

Example 3

Previous examples reviewed the physical effects of RFA-mediated denervation in ex vivo tissue models. Example 3 discusses an in vivo longitudinal analysis of changes that occur along the ablated nerve in response to CRF and SRF procedures, demonstrating in vivo that CRF generates a larger lesion as measured by both histology and MRI, i.e., larger lesions in both length and volume.

The rodent sciatic nerve was selected as the ablation target, as it is of comparable size to human nerves of interest and provides both sensory and motor innervation.

Moreover, the rodent allows for the feasible evaluation of changes that are suspected to occur over months and years in the human, since 2 weeks in the lifespan of a rodent is approximately equivalent to 1 human year. One group of Lewis rat sciatic nerves were treated to recommended clinical parameters of SRF (90 s, 80° C., 22 gauge, 5 mm active tip probe) or CRF (150 s, 60° C., 17 gauge, 2 mm active tip probe), and nerves were harvested immediately post-ablation for histological analysis. Following fixation in 10% formalin, sciatic nerves were embedded in paraffin blocks, and longitudinal sections were stained in H&E. Another group of Lewis rat sciatic nerves were exposed to optimized levels of SRF (50 s, 80° C., 22 gauge, 5 mm active tip probe) or CRF (80 s, 60° C., 17 gauge, 2 mm active tip probe), to ensure long-term survival without severe adverse events. This group of surviving rats was tracked and assessed for structural modifications at the lesion zone via hematoxylin and eosin (H&E) histological analysis, immunohistochemistry (CD11b, macrophage staining), lesion progression via magnetic resonance imaging (MRI—using a 9.4T Bruker scanner), and lesion visibility at necropsy (caliper measurements). Volumetric analysis of magnetic resonance scans was performed using Image J to quantify the size of the lesions created by both SRF and CRF.

Figure 17:
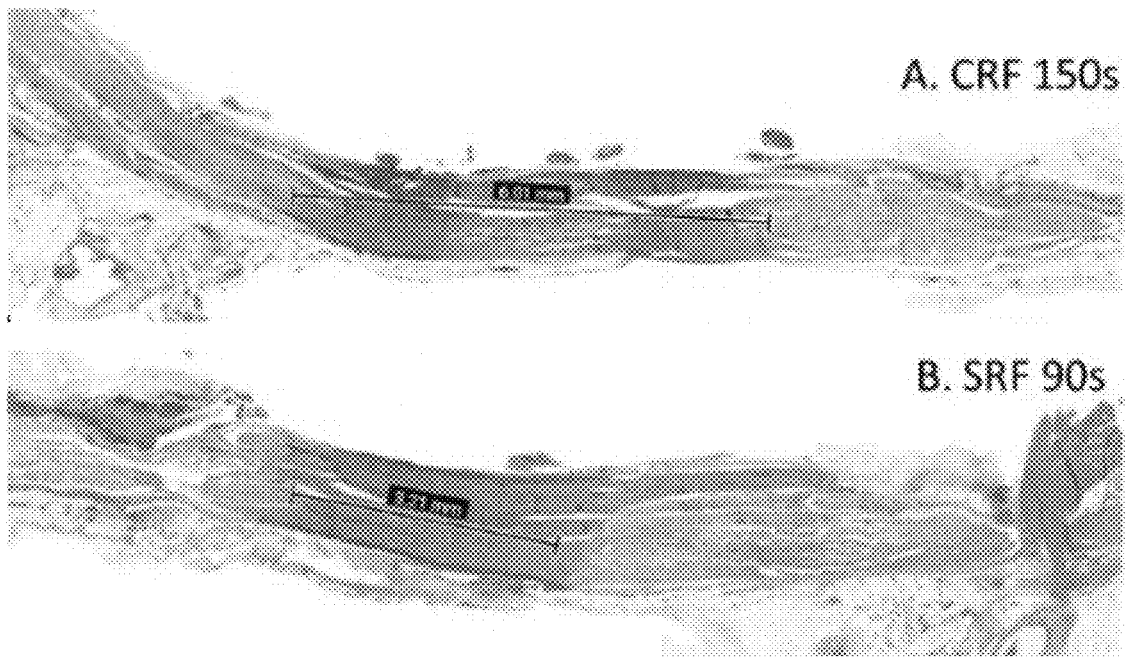
FIG. 17 shows images of rat sciatic nerve tissue stained with hemytoxalin and eosin (H&E). Top) H&E image of tissue treated with CRF ablation for 150 seconds, having a lesion of 6.01 mm in length. Bottom) H&E image of tissue treated with SRF ablation for 90 seconds, having a lesion of 3.21 millimeters in length.
Figure 18:
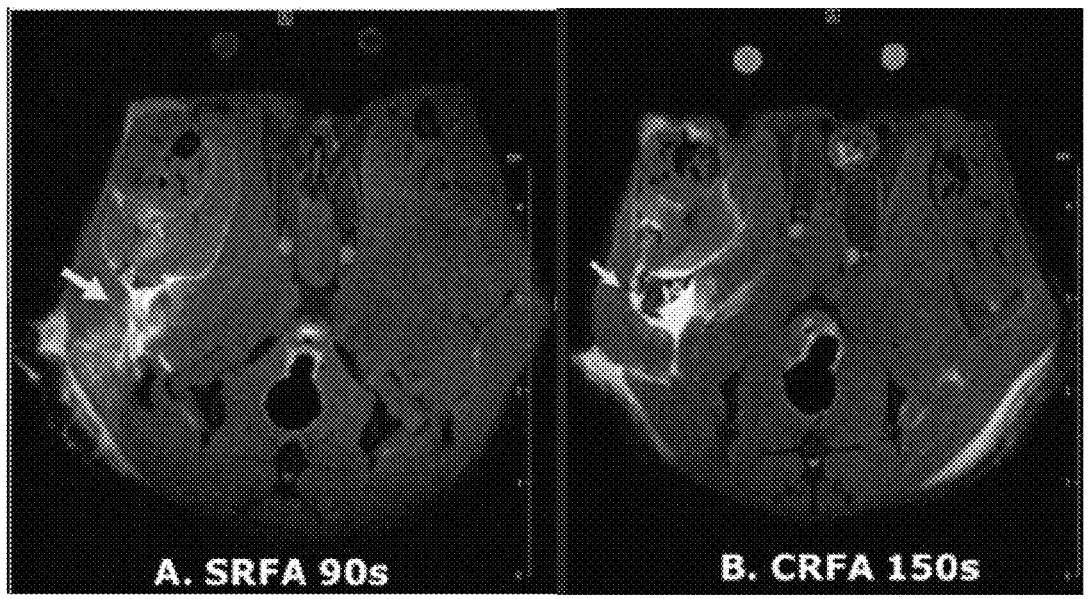
FIG. 18 shows magnetic resonance images (MRI) of the rat sciatic nerve after treatment with SRF versus CRF, demonstrating that lesions (marked by arrows) formed by CRF are larger than those formed by SRF. (Left) MR scan of tissue treated with SRF ablation for 90 seconds. (Right) MR scan of tissue treated with CRF ablation for 150 seconds.

Using H&E staining to assess the structure of lesions created on the sciatic nerve by clinical RFA parameters, CRF ablations were observed to produce lesions with an average lesion length of 4.75±1.07 mm, which is approximately 1.5× longer than SRF lesions (FIG. 17). It was also observed within the ablation zone a region of lesser damage (pink) flanked by two regions of more severe damage (purple), which parallels the thermal profile of cooled RF lesions observed ex vivo. Preliminary volumetric analysis from MRI scans of rats that were treated with clinical RFA parameters (FIG. 18) also suggest that CRF ablations have a larger volume compared to SRF ablations (1311.8±101.8 mm³ in CRF vs. 1054.7 mm³ in SRF, n=2). Caliper measurements at the time of ablation (t=0) also demonstrate that CRF ablations produce significantly larger lesions (9.83±0.28 mm) when compared to SRF lesions (4.33±0.28 mm). Additionally, by 14 days post-ablation or 1 human year, the visible SRF lesion had resolved (0±0 mm), whereas the CRF lesions persisted (5.83±0.76 mm). Finally, preliminary staining of nerves 7 days post ablation with CD11 b markers suggests that SRF treated animals have increased macrophage infiltration compared with CRF treated animals at the same time point.

These results have begun to identify the time frame in which nerves repair following RF ablation, and provide preliminary structural evidence as to the underlying mechanistic differences associated with different RF techniques. These results also provide in vivo evidence that CRF generates a larger lesion as measured by histology and MRI, and that these lesions appear to persist longer at the ablation site, as indicated by caliper measurements. The observation of lesions at day 14 (1 human year) only in CRF treated animals (and not in SRF treated animals) provides a preliminary explanation as to why patients experience a return of pain sooner following treatment with SRF, and not with CRF. Furthermore, an increased presence of CD11b macrophage staining at day 7 in the nerves ablated with SRF suggests that these nerves undergo immune repair faster, providing another explanation for why patients treated with SRF return to pain sooner.

Example 4

Figure 19:
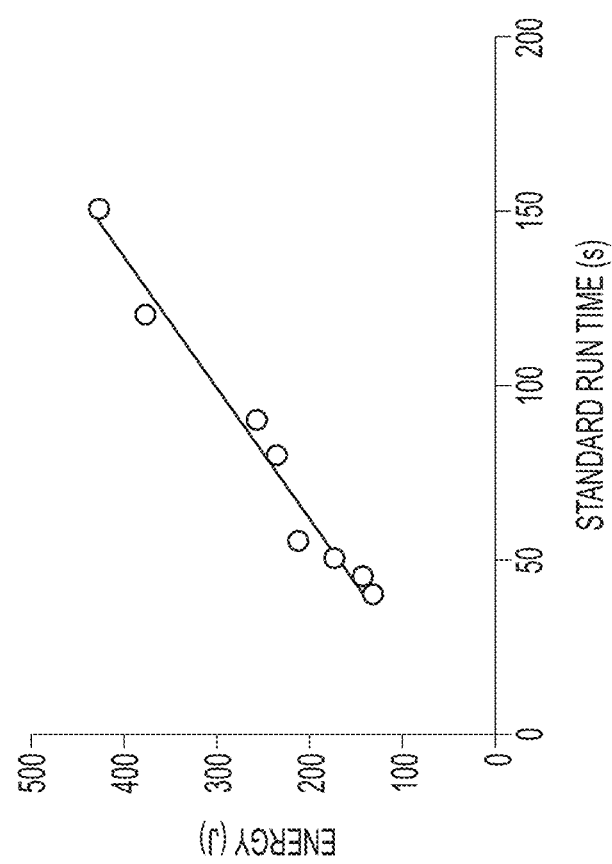
FIG. 19 is a graph showing the amount of energy released (joules) during standard RF at various run times, with a linear trendline extending through the data. $r^2=0.9714$.

In a clinical setting, standard RF ablation is typically run for about 90 seconds, whereas cooled RF is run for about 150 seconds. A typical, 90 second clinical run of standard RF releases about 258 joules of energy, whereas a typical, 150 second clinical run of cooled RF releases about 943 joules of energy (about 3.7 times more energy). This increased energy results in better modulation of pain, as described above. In the past, it has not been entirely clear if standard RF could be run for longer periods of time to release similar amounts of energy as cooled RF. Extrapolation of the amount of energy released during typical runs of standard RF (FIG. 19) demonstrates that standard RF would need to run for about 340 seconds to achieve the approximately 943 joules of energy released during a clinical run of cooled RF.

Figure 20:
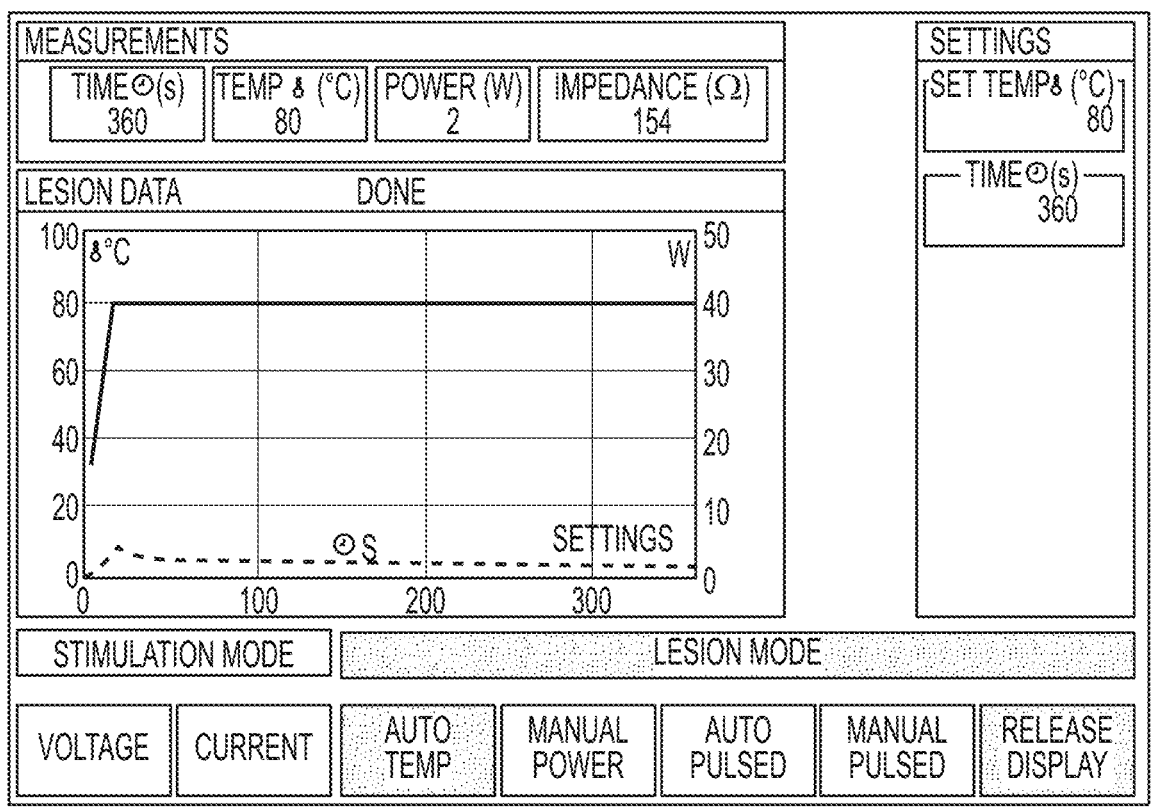
FIG. 20 shows the output display for an extended run (360 second) standard RF experiment.

This extrapolation was used to set up a rat experiment comparing energy released during standard and cooled RF over various run times. For the experiment, four standard RF ablations were run for 360 seconds each (2 rats, bilateral hind leg ablation). The output display of FIG. 20 shows some of the conditions used during the experiment. Energy delivery was measured, lesion size and charring were evaluated, and tissues were collected for histology. Any power changes and/or generator safety shut-offs that occurred during the run were noted.

Figure 21:
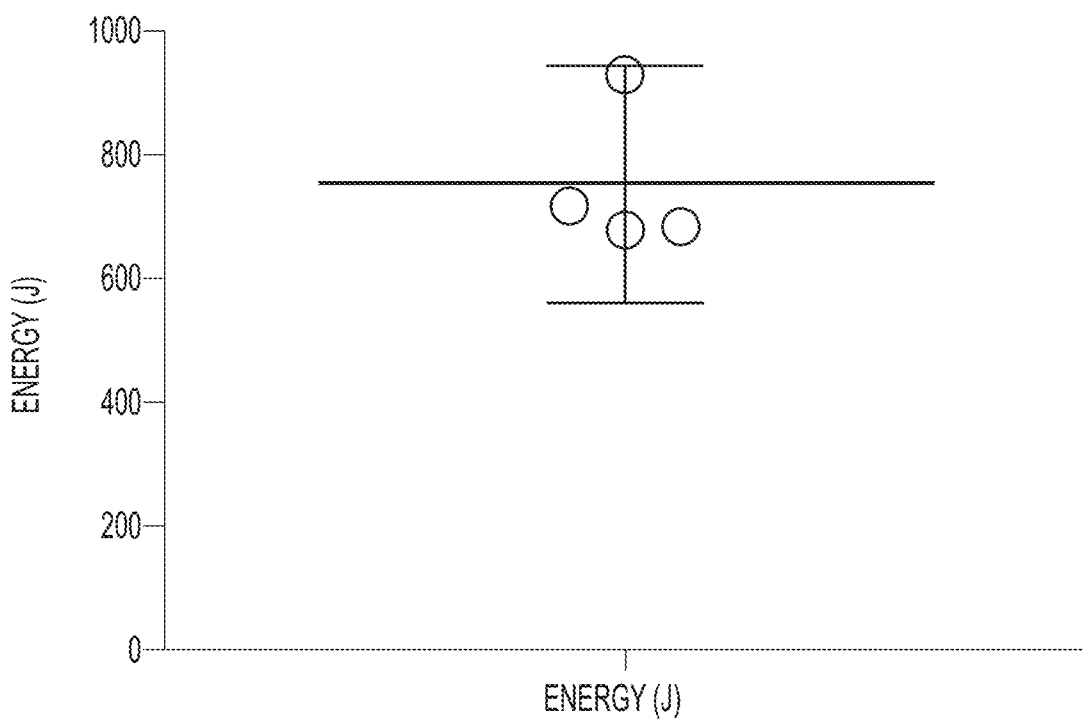
FIG. 21 is a scatter plot of the average total energy output of the generator when a standard RF ablation is run for 360 seconds (n=4). Central bar indicates mean, upper and lower bars indicate standard deviation.
Figure 22:
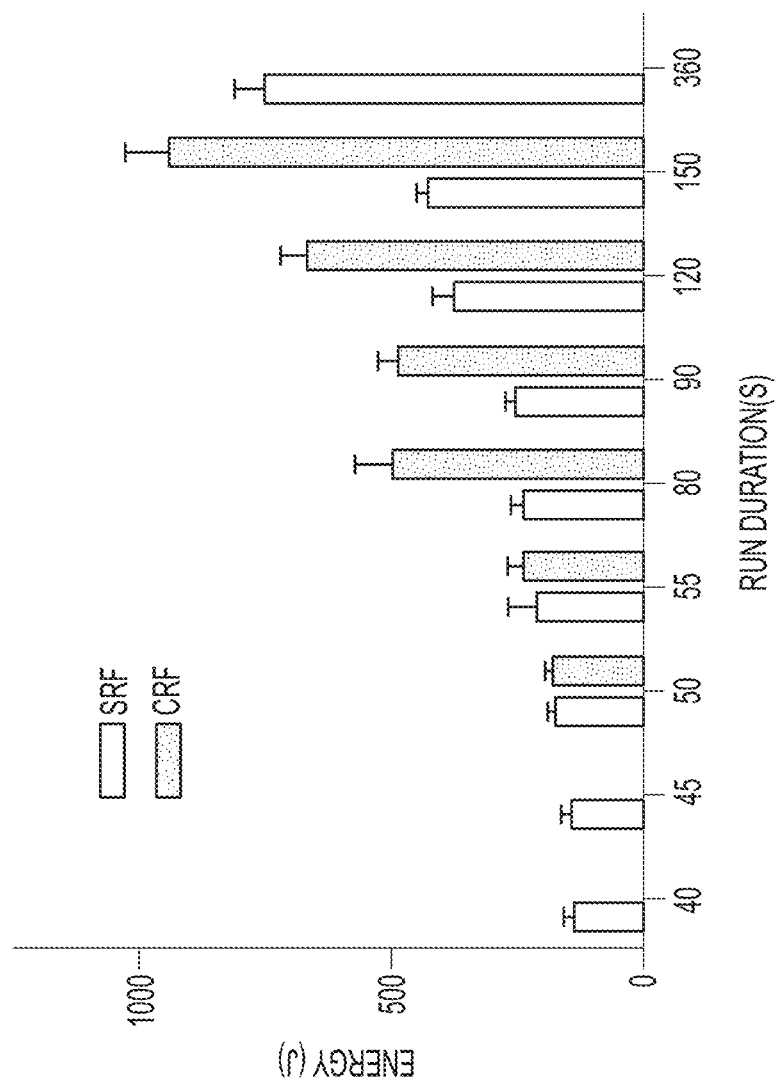
FIG. 22 is a bar graph showing the amount of Lewis energy compiled (joules) at various run durations, for standard RF (SRF) and cooled RF (CRF). Bars indicate mean±standard error.
Figure 23:
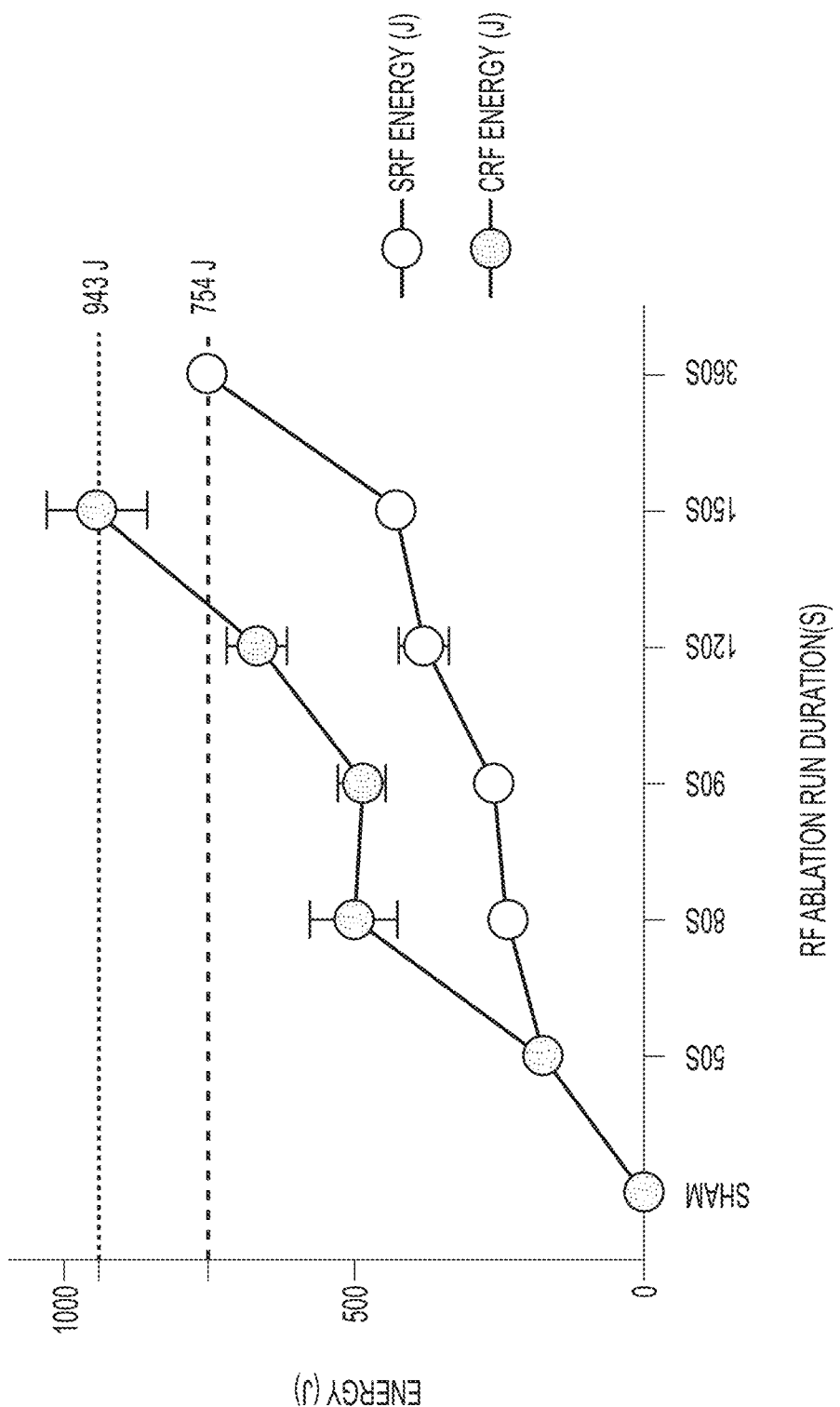
FIG. 23 is a line graph showing the amount of energy delivered (joules) at various run durations for standard RF and cooled RF. Dots indicate mean±standard error.

The mean energy delivered over the experimental 360 second standard RF run was 754 joules (FIG. 21), far less than the amount of energy released during cooled RF using standard clinical run times (943 joules over 150 seconds). The data for amount of energy released under standard RF for 360 seconds is compared to the amount of energy released over other time periods in Tables 3 and 4, below. Bold indicates the clinical standard conditions. Underlining indicates run time optimized for rodent models. Even using the rodent optimization parameters described above, cooled RF still delivers about 3.5 times more energy than standard RF at the rodent-optimized parameters. These data are presented in bar graph form at FIG. 22, and in line graph form at FIG. 23.

TABLE 3

Energy released by standard RF at various run times.

STANDARD RF

| Run Duration (s) | 40  | 45  | _50_ | 55  | 80 | 90 | 120  | 150  | 360   |
|---|---|---|---|---|---|---|---|---|---|
| N                | 3   | 6   | _13_ | 6   | 5  | 13 | 5    | 5    | 4     |
| ENERGY (J)       | 132 | 144 | _174_ | 213 | 235 | 258 | 378  | 427  | 754   |
| (% reduction)    | 49% | 44% | _33%_ | 17% | 9% |        | +47% | +65% | +292% |

TABLE 4

Energy released by cooled RF at various run times.

COOLED RF

| Run Duration (s) | 50  | 55  | 60  | 65  | 70  | 75  | _80_ | 90  | 120 | 150 |
|---|---|---|---|---|---|---|---|---|---|---|
| N                | 5   | 14  | 6   | 6   | 2   | 2   | _6_  | 3   | 5   | 13 |
| ENERGY (J)       | 175 | 237 | 361 | 344 | 427 | 444 | _498_ | 485 | 667 | 943 |
| (% reduction)    | 81% | 75% | 62% | 64% | 55% | 53% | _46%_ | 48% | 30% |        |

Figure 24:
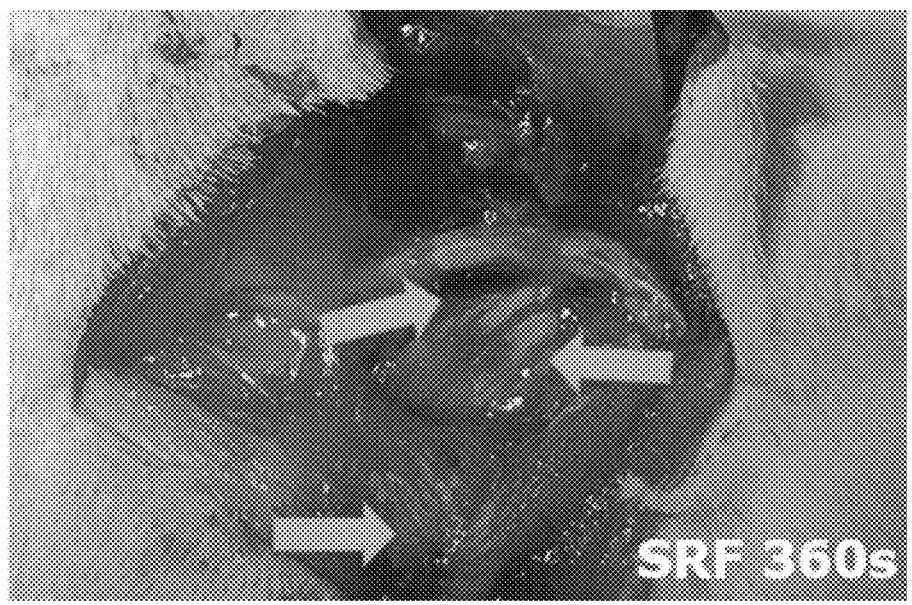
FIG. 24 is a photograph illustrating charring and swelling associated with extended duration standard RF (run time, 360 seconds).
Figure 25:
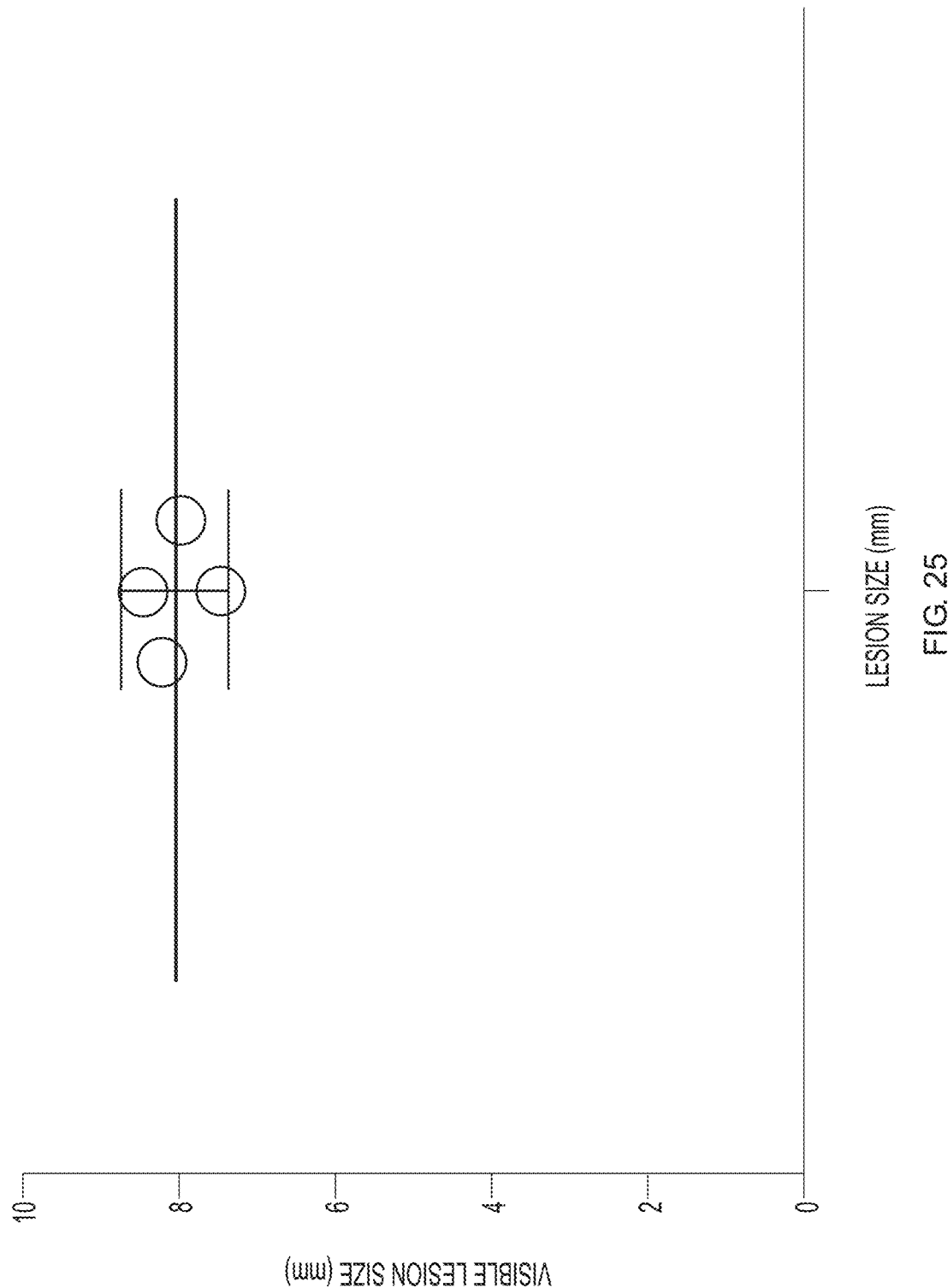
FIG. 25 is a scatter plot showing the lesion size resulting from standard RF under extended run time conditions (360 seconds).
Figure 26:
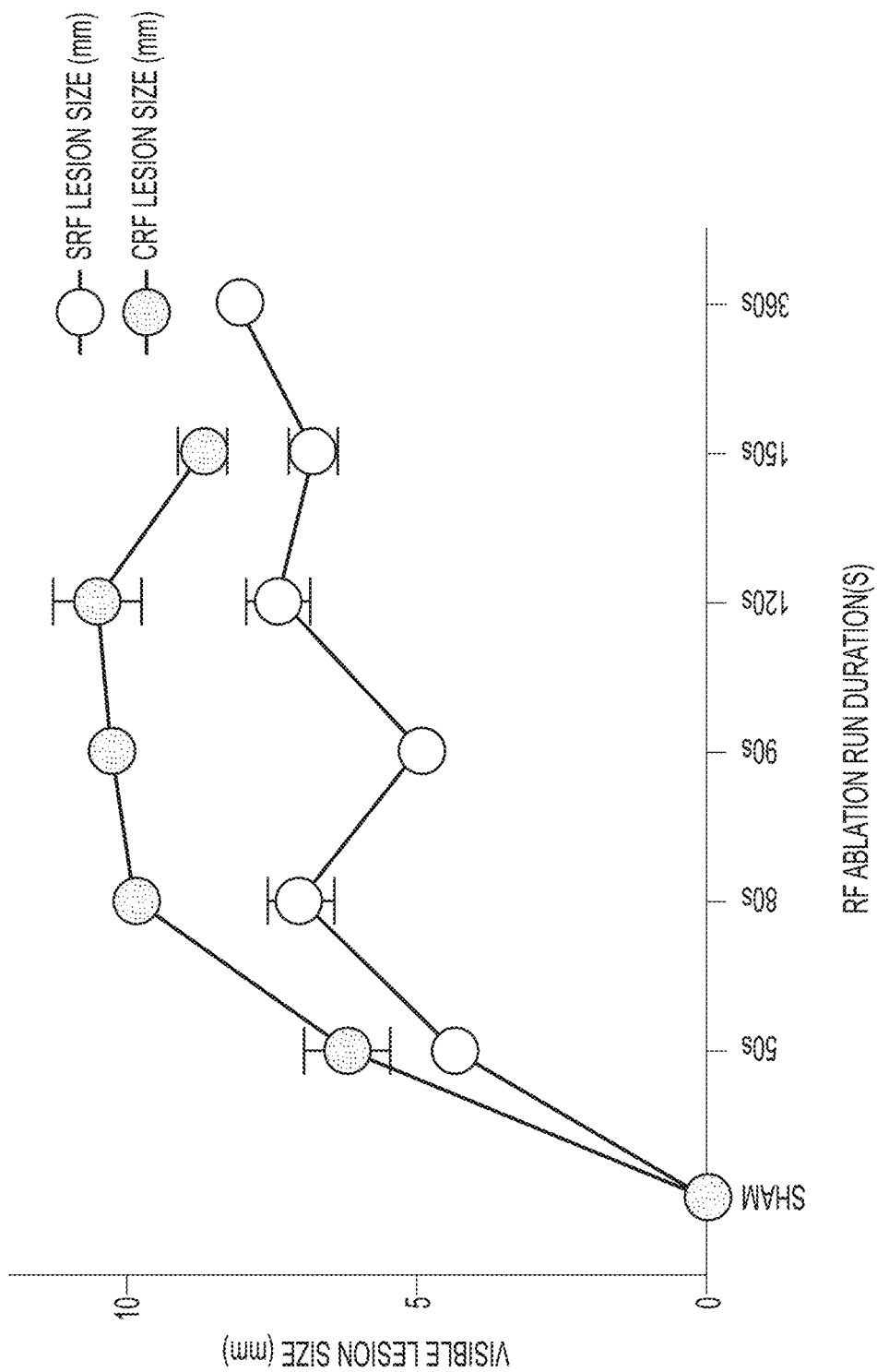
FIG. 26 is a line graph showing the lesion sizes (mm) resulting from various run durations under both cooled and standard RF.

Tissue subjected to standard RF for 360 seconds generally showed significant swelling and charring (FIG. 24, at arrows), and the resulting lesions were, on average, about 8 millimeters long (FIG. 25). Compiled lesion size data is shown at FIG. 26. The lesion size attained by running standard RF for 360 seconds is still smaller than the lesion size attained by running cooled RF under clinical conditions (90 seconds). As such, extended duration standard RF results in tissue dehydration and charring of tissue, which lowers impedance, resulting in improper or incomplete ablation, and smaller lesions (less likely to successfully ablate target nerves) than clinical standard cooled RF.

Example 5

Wider and longer active tip probes were evaluated under both cooled and standard RF. For cooled RF, the experimental probe was 17 gauge with a 4 millimeter active tip length (by comparison, clinical standard probes are about 17 gauge with about a 2 millimeter active tip length, though the size may vary depending on the anatomical site being ablated). For standard RF, the probe evaluated in this example was 18 gauge with a 10 millimeter active tip length (by comparison, clinical standard is about 22 gauge with about a 5 millimeter active tip length, though the size may vary depending on the anatomical site being ablated). Differences between standard and cooled RF were assessed in terms of energy output/delivery, lesion length, and nerve function using the wider and longer active tip probes. A total of 8 ablations were performed (4 rats, 2 rats per experimental group, bilateral hind leg ablation). Data were obtained at T=0 (just after ablation). Experimental groups included: clinical SRF (90 seconds), optimized SRF (50 seconds), clinical CRF (150 seconds), optimized CRF (80 seconds).

Figure 27:
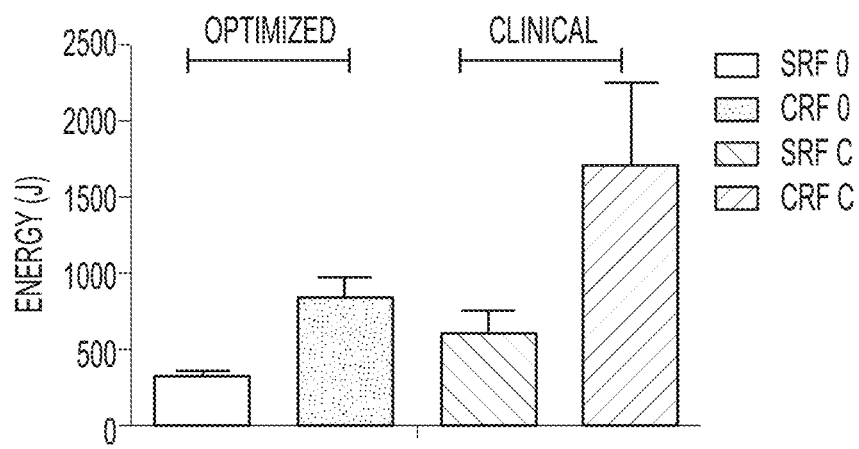
FIG. 27 is a bar graph showing energy delivered (joules) using larger probes. N=2 ablations per group. Bars indicate mean±standard error.
Figure 28:
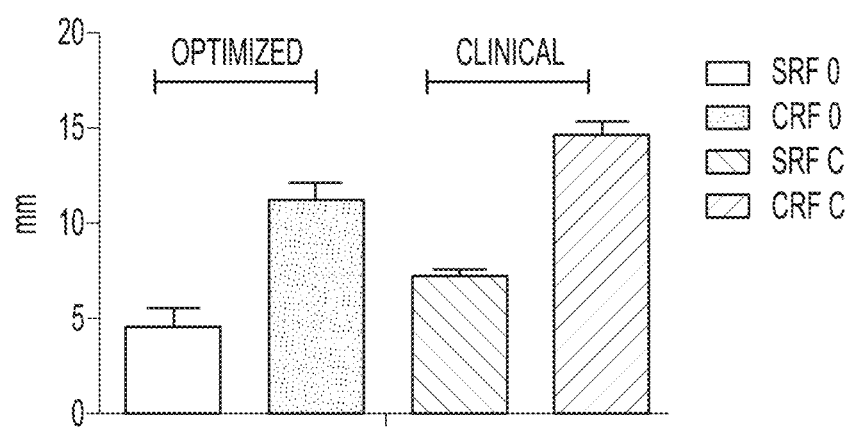
FIG. 28 is a bar graph showing the visible lesion size at T=0 after ablation. N=2 ablations per group. Bars indicate mean±standard error.
Figure 29:
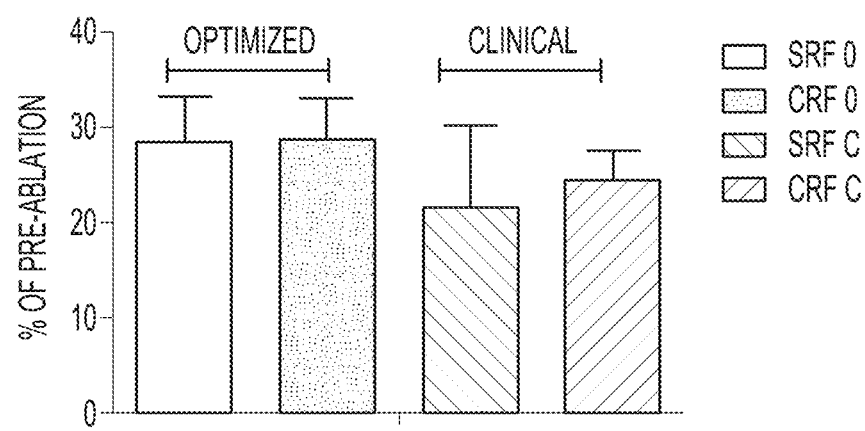
FIG. 29 is a bar graph showing the EMG values as a percent of the pre-ablation EMG values, at T=0 after ablation. N=2-3 ablations per group. Bars indicate mean±standard error.

FIG. 27 shows the amount of energy (joules) delivered for each group using the larger probes. FIG. 28 shows the visible lesion size (mm), and FIG. 29 shows the EMG as a percent of pre-ablation. Under both clinical and optimized run durations, cooled RF generates greater energy compared to standard RF (FIG. 27), cooled RF ablation induces larger lesions compared to standard RF (FIG. 28). FIG. 29 shows that immediately post ablation, standard and cooled RF ablations have a comparable reduction in the EMG-signal compared to the pre-ablation EMG-signal.

The embodiments of the invention described above are intended to be exemplary only. The scope of the invention is therefore intended to be limited solely by the scope of the appended claims. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Vania Apkarian et al. Neural mechanisms of pain and alcohol dependence. Pharmacol Biochem Behav. 2013 November; 112: 34-41.
2. Chaplan S R, Bach F W, Pogrel J W, Chung J M, Yaksh T L. Quantitative assessment of tactile allodynia in the rat paw. J Neurosci Methods. 1994 July; 53(1): 55-63.
3. Crone T, video, "What is cooled radiofrequency? The physics of RF ablation." available online at https://www.cooledrf.london/what-is-coolief-new.html (last accessed Aug. 24, 2018).
4. Choi et al. Internal-specific Morphological Analysis of Sciatic Nerve Fibers in a RF-induced Animal Neuropathic Pain Model. PLOS One. 2013.
5. Davis T, Loudermilk E, DePalma M, et al. Prospective, Multicenter, Randomized, Crossover Clinical Trial Comparing the Safety and Effectiveness of Cooled Radiofrequency Ablation With Corticosteroid Injection in the Management of Knee Pain From Osteoarthritis. Regional Anesthesia and Pain Medicine. 2018; 43(1):84-91. doi:10.1097/AAP.0000000000000690.
6. English A, Chen Y, Carp J S, Wolpaw J R, Chen X Y. Recovery of electromyographic activity after transection and surgical repair of the rat sciatic nerve. J Neurophysiol. 2007 February; 97(2): 1127-34. Epub 2006 Nov. 22. doi:10.1152/jn.01035.2006
7. Han J S, Adwanikar H, Li Z, Ji G, Neugebauer V. Facilitation of synaptic transmission and pain responses by CGRP in the amygdala of normal rats. Molecular Pain. 2010 Feb. 8; 6:10. doi:10.1186/1744-8069-6-10.
8. Halyard Health, "Halyard Health Announces New Data Supporting COOLIEF* Cooled RF for the Treatment of Chronic Osteoarthritis Knee Pain," Sep. 18, 2017, available at https://www.halyardhealth.com/about-us/halyard-news/2017/september/halyard-health-announces-new-data-supporting-coolief-cooled-rf-for-the-treatment-of-chronic-osteoarthritis-knee-pain.aspx
9. Larson A, Brown D, El-Atrash S, Walser M. Pain threshold changes in adjuvant-induced inflammation: A possible model of chronic pain in the mouse. Pharmacology Biochemistry and Behavior. 1986 January; 24(1): 49-53. doi:10.1016/0091-3057(86)90043-2.

What is claimed is:

1. A system for controlling energy delivered to an area of tissue during a treatment procedure, the system including:
   a device for delivering energy to the area of tissue;
   an energy generator for generating and supplying energy to the device; and
   a controller for controlling an amount of energy generated by the energy generator and delivered to the area of tissue by the device, wherein controlling the amount of energy delivered to the area of tissue alters a primary zone of the area of tissue to a first level, alters a secondary zone of the area of tissue to a second level, and alters a tertiary zone of the area of tissue to a third level, wherein the first level, the second level, the third level, or a combination thereof is predetermined, and wherein a coverage area of the primary zone, the secondary zone, the tertiary zone, or a combination thereof is predetermined;
   wherein the tertiary zone surrounds the secondary zone, and the secondary zone surrounds the primary zone;
   wherein the secondary zone increases the coverage area of the primary zone by a factor ranging from 1.25 to 15;
   wherein the primary zone is adjacent the device, the secondary zone is adjacent the primary zone, and the tertiary zone is adjacent the secondary zone; and
   wherein the first level of tissue alteration is associated with from 75 percent to 100 percent coagulation of proteins, the second level of tissue alteration is associated with from 25 percent to less than 75 percent coagulation of proteins, and the third level of tissue alteration is associated with greater than 0 percent but less than 25 percent coagulation of proteins.

2. The system of claim 1, wherein the device for delivering energy to the area of tissue is a percutaneous probe.

3. The system of claim 1, wherein the device for delivering energy is a cooled radiofrequency probe, and wherein the cooled radiofrequency probe includes a sensing device for sending a signal to the controller for controlling the amount of energy generated and/or operation of a cooling mechanism of the cooled radiofrequency probe to adjust a property of the cooled radiofrequency probe and/or the area of the tissue.

4. The system of claim 1, wherein the coverage area for the primary zone, the secondary zone, the tertiary zone, or a combination thereof is determined via a relationship between the amount of energy delivered to the area of tissue, an amount of time during which the energy is delivered, a waveform type, device placement, device location, device dimensions, surgical approach, a temperature at which the energy is delivered, or a combination thereof.

5. The system of claim 1, wherein the first level, the second level, the third level, or a combination thereof is determined via a relationship between the amount of energy delivered to the area of tissue, an amount of time during which the energy is delivered, a waveform type, device placement, device location, device dimensions, surgical approach, a temperature at which the energy is delivered, or a combination thereof.

6. The system of claim 1, wherein the first level corresponds to a greater extent of tissue alteration, cell type alteration, biochemical signaling alteration, or a combination thereof compared to the second level, and wherein the second level corresponds to a greater extent of tissue alteration cell type alteration, biochemical signaling alteration, or a combination thereof compared to the third level.

7. The system of claim 1, wherein the treatment procedure is a denervation procedure, wherein a physical lesion associated with denervation is induced in the primary zone, wherein a lesser extent of denervation is induced in the secondary zone compared to the primary zone, wherein one or more biochemical changes and/or physiological responses are induced in the tertiary zone, or a combination thereof.

8. The system of claim 7, wherein the one or more biochemical changes and/or physiological responses includes changes in levels of perineurial collagen coagulation, epineurial collagen coagulation, endoneurial collagen coagulation, coagulative necrosis, vascular necrosis, axonal degeneration, inflammation, subacute histiocytosis, hypertrophy, hyperplasia, immune cell activation, schwann cell infiltration, nerve fibrosis, macrophage infiltration, growth cone sprouting, structural integrity, sensory threshold, biochemical signaling, cell body response, dorsal root ganglia response, or a combination thereof.

9. A method for controlling energy delivered to an area of tissue during a treatment procedure, the method including the steps of:
   inserting a device for delivering energy adjacent the area of tissue to be treated;
   generating and supplying energy to the device via an energy generator; and
   controlling an amount of energy generated by the energy generator and delivered to the area of tissue by the device via a controller, wherein controlling the energy delivered to the area of tissue alters a primary zone of the area of tissue to a first level, alters a secondary zone of the area of tissue to a second level, and alters a tertiary zone of the area of tissue to a third level, wherein the first level, the second level, the third level, or a combination thereof is predetermined, and wherein a coverage area of the primary zone, the secondary zone, the tertiary zone, or a combination thereof is predetermined;
   wherein the tertiary zone surrounds the secondary zone, and the secondary zone surrounds the primary zone;
   wherein the secondary zone increases the coverage area of the primary zone by a factor ranging from 1.25 to 15;
   wherein the primary zone is adjacent the device, the secondary zone is adjacent the primary zone, and the tertiary zone is adjacent the secondary zone; and
   wherein the first level of tissue alteration is associated with from 75 percent to 100 percent coagulation of proteins, the second level of tissue alteration is associated with from 25 percent to less than 75 percent coagulation of proteins, and the third level of tissue alteration is associated with greater than 0 percent but less than 25 percent coagulation of proteins.

10. The method of claim 9, further comprising delivering about 25 joules to about 100 kilojoules of energy to the area of tissue.

11. The method of claim 9, wherein the device for delivering energy is a cooled radiofrequency probe and the energy delivered to the area of tissue is cooled radiofrequency energy, and wherein the method further comprises sending a signal from a sensing device on the cooled radiofrequency probe to the controller for controlling the amount of energy generated and/or operation of a cooling mechanism of the cooled radiofrequency probe to adjust a property of the cooled radiofrequency probe and/or the area of the tissue.

12. The method of claim 9, further comprising determining the coverage area for the primary zone, the secondary zone, the tertiary zone, or a combination thereof based on a relationship between the amount of energy delivered to the area of tissue, an amount of time during which the energy is delivered, a waveform type, device placement, device location, device dimensions, surgical approach, a temperature at which the energy is delivered, or a combination thereof.

13. The method of claim 9, further comprising determining the first level, the second level, the third level, or a combination thereof based on a relationship between the amount of energy delivered to the area of tissue, an amount of time during which the energy is delivered, a waveform type, device placement, device location, device dimensions, surgical approach, a temperature at which the energy is delivered, or a combination thereof.

14. The method of claim 9, wherein the first level corresponds to a greater extent of tissue alteration, cell type alteration, biochemical signaling alteration, or a combination thereof compared to the second level, and wherein the second level corresponds to a greater extent of tissue alteration, cell type alteration, biochemical signaling alteration, or a combination thereof compared to the third level.

15. The method of claim 9, wherein the secondary zone increases an area of effective denervation of the primary zone by a factor ranging from about 1.25 to about 15.

16. The method of claim 9, wherein the treatment procedure is a denervation procedure, the method further comprising inducing a physical lesion associated with denervation in the primary zone, inducing a lesser extent of denervation in the secondary zone compared to the primary zone, inducing one or more biochemical changes and/or physiological responses in the tertiary zone, or a combination thereof.

17. The method of claim 16, wherein the one or more biochemical changes and/or physiological responses includes changes in levels of perineurial collagen coagulation, epineurial collagen coagulation, endoneurial collagen coagulation, coagulative necrosis, vascular necrosis, axonal degeneration, inflammation, subacute histiocytosis, hypertrophy, hyperplasia, immune cell activation, schwann cell infiltration, nerve fibrosis, macrophage infiltration, growth cone sprouting, structural integrity, sensory threshold, biochemical signaling, cell body response, dorsal root ganglia response, or a combination thereof.

18. The method of claim 9, wherein the method further comprises providing pain relief to a subject.

\* \* \* \* \*